United States Patent [19]

Georgiou et al.

[11] Patent Number: 5,348,867
[45] Date of Patent: Sep. 20, 1994

[54] EXPRESSION OF PROTEINS ON BACTERIAL SURFACE

[75] Inventors: George Georgiou, 11501 Juniper Ridge Dr., Austin, Tex. 78759; Joseph A. Francisco; Charles F. Earhart, both of Austin, Tex.

[73] Assignee: George Georgiou, Austin, Tex.

[21] Appl. No.: 794,731

[22] Filed: Nov. 15, 1991

[51] Int. Cl.$^5$ .................. C12P 21/06; C12P 21/04; C12N 15/00; C12N 1/20
[52] U.S. Cl. .................. 435/69.7; 435/69.8; 435/71.1; 435/71.2; 435/172.1; 435/252.1; 435/252.3; 435/252.33; 435/320.1; 536/23.4
[58] Field of Search .............. 536/27; 435/69.7, 69.8, 435/71.1, 71.2, 172.1, 252.1, 252.3, 252.33, 320.1

[56] References Cited

U.S. PATENT DOCUMENTS

| | | | |
|---|---|---|---|
| 3,791,932 | 2/1974 | Schuurs et al. | 195/103.5 R |
| 3,949,064 | 4/1976 | Bornstein et al. | 424/1 |
| 4,174,384 | 11/1979 | Ullman et al. | 424/8 |
| 4,596,792 | 6/1986 | Vyas | 514/21 |
| 4,599,230 | 7/1986 | Milich et al. | 424/89 |
| 4,599,231 | 7/1986 | Milich et al. | 424/89 |
| 4,601,903 | 7/1986 | Frasch | 424/92 |
| 4,608,251 | 8/1986 | Mia | 424/85 |
| 5,223,409 | 6/1993 | Ladner et al. | 435/69.7 |

OTHER PUBLICATIONS

Pugsley, A. P. et al., *Microbiological Reviews*, 57: 50–108, 1993.
Dudega, B. et al., *FEMS Microbiology Letters*, 108: 353–360, 1993.
Laukkanen, M. L. et al., *Protein Engineering*, 6 (4): 449–454, 1993.
Francisco, J. A. et al., *Bio/Technology*, 11: 491–495, 1993.
Francisco, J. A. et al., *PNAS*, 89: 2713–2717, Apr. 1992.
Charbit, A. et al., *The EMBO Journal*, 5(11): 3029–3037, 1986.
Klauser, T. et al., *The EMBO Journal*, 9(6): 1991–2000, 1990.
Pistor, S. et al., *Res. Microbiol.*, 141 (7–8): 879–881, 1990.
Agterberg et al., Gene, 59:145–150, 1987.
Barbas et al., Proc. Natl. Acad. Sci. USA, 88:7978–7982, 1991.
Bardwell et al., Cell, 67:581–589, 1991.
Bolivar et al., Gene, 2:95–113, 1977.
Bosch et al., J. Mol. Biol., 189:449–455, 1986.
Bosch et al., Mol. Gen. Genet., 216:144–148, 1989.
Breitling et al., Gene, 104:147–153, 1991.
Chang et al., Nature, 275:617–624, 1978.
Charbit et al., J. Bacter., 173(1):262–275, 1991.
Clackson et al., Nature, 352:624–628, 1991.
De Libero & Kaufmann, J. Immun., 137(8):2688–2694, 1986.
Ehrmann et al., Proc. Natl. Acad. Sci. USA, 87:7574–7578, 1990.
Dougan et al., Ad. Vet. Sci. Compara. Med., 33:271–300, 1989.
Filloux et al., EMBO J., 9(13):4323–4329, 1990.
Freudl et al., EMBO J., 4(13):3593–3598, 1985.
R. Freudl, Gene, 82:229–236, 1989.
Goeddel et al., Nature, 281:544–548, 1979.
Ghrayeb & Inouye et al., J. Biol. Chem., 259(1):463–467, 1984.
Huse et al., Science, 246:1275–1281, 1989.

(List continued on next page.)

Primary Examiner—Robert J. Hill, Jr.
Assistant Examiner—Marianne Porta Allen
Attorney, Agent, or Firm—Arnold, White & Durkee

[57] ABSTRACT

The invention relates to a method for producing stable, surface-expressed polypeptides from recombinant gram-negative bacterial cell hosts. A tripartite chimetic gene and its related recombinant vector include separate DNA sequences for directing or targeting and translocating a desired gene product from a cell periplasm to the external cell surface. A wide range of polypeptides may be efficiently surface expressed, including β-lactamase and alkaline phosphatase. Full enzyme activity is maintained and the proteins remain anchored to the bacterial outer membrane surface.

19 Claims, 10 Drawing Sheets

OTHER PUBLICATIONS

Itakura et al., Science, 198:1056–1063, 1977.
Jacobs et al., Gene, 83:95–103, 1989.
Klose et al., J. Biol. Chem., 263(26):13291–13296, 1988.
Klose et al., J. Biol. Chem., 263(25):13297–13302, 1988.
Kornacker & Pugsley, Mol. Micro. 4(1):73–85, 1989.
Kornacker & Pugsley, Mol. Micro. 4(7):1101–1109, 1990.
Kronvall et al., Infect. Immun., 25(1):1–10, 1979.
Murphy & Klebba, J. Bac., 171(11):5894–5900, 1989.
Newton et al., Science, 244:70–72, 1989.
O'Callaghan et al., Antimicrobial Agents and Chemotherapy, 1(4):283–288, 1972.
Orlandi et al., Proc. Natl. Acad. Sci. USA, 86:3833–3837, 1989.
Powers et al., Biotechnology and Bioengineering, 33:173–182, 1989.
Amram Samuni, Analytical Biochemistry, 63:17–26, 1975.
Sastry et al., Proc. Natl. Acad. Sci. USA, 86:5728–5732, Aug. 1989.
Siebenlist et al., Cell, 20:269–281, Jun. 1980.
Skerra & Plückthun, Science, 24:1038–1040, May 1988.
Stover et al., Nature, 351:456–460, Jun. 6, 1991.
Thiry et al., Applied and Environmental Microbiology, 55(5):984–993, Apr. 1989.
Tsao et al., Bio/Technology, pp. 1330–1333, Nov. 1988.
Vieira & Messing, Gene, 19:259–268, 1982.
Yamaguchi et al., Cell, 53:423–432, May 6, 1988.
Charles & Dougan, Trends in Biochemistry, 1990.

```
ATGAAAGCTA CTAAACTGGT ACTGGGCGCG GTAATCCTGG GTTCTACTCT 50
GCTGGCAGGT TGCTCCAGCA ACGCTAAAAT CGATCAGGGA ATTAACCCGT 100
ATGTTGGCTT TGAAATGGGT TACGACTGGT TAGGTCGTAT GCCGTACAAA 150
GGCAGCGTTG AAAACGGTGC ATACAAAGCT CAGGGCGTTC AACTGACCGC 200
TAAACTGGGT TACCCAATCA CTGACGACCT GGACATCTAC ACTCGTCTGG 250
GTGGCATGGT ATGGCGTGCA GACACTAAAT CCAACGTTTA TGGTAAAAAC 300
CACGACACCG GCGTTTCTCC GGTCTTCGCT GGCGGTGTTG AGTACGCGAT 350
CACTCCTGAA ATCGCTACCC GTCTGGAATA CCAGTGGACC AACAACATCG 400
GTGACGCACA CACCATCGGC ACTCGTCCGG ACAACGGAAT TCCGGGTCAC 450
CCAGAAACGC TGGTGAAAGT AAAAGATGCT GAAGATCAGT TGGGTGCACG 500
AGTGGGTTAC ATCGAACTGG ATCTCAACAG CGGTAAGATC CTTGAGAGTT 550
TTCGCCCCGA AGAACGTTTT CCAATGATGA GCACTTTTAA AGTTCTGCTA 600
TGTGGCGCGG TATTATCCCG TGTTGACGCC GGGCAAGAGC AACTCGGTCG 650
CCGCATACAC TATTCTCAGA ATGACTTGGT TGAGTACTCA CCAGTCACAG 700
AAAAGCATCT TACGGATGGC ATGACAGTAA GAGAATTATG CAGTGCTGCC 750
ATAACCATGA GTGATAACAC TGCGGCCAAC TTACTTCTGA CAACGATCGG 800
AGGACCGAAG GAGCTAACCG CTTTTTTGCA CAACATGGGG GATCATGTAA 850
CTCGCCTTGA TCGTTGGGAA CCGGAGCTGA ATGAAGCCAT ACCAAACGAC 900
GAGCGTGACA CCACGATGCC TGCAGCAATG GCAACAACGT TGCGCAAACT 950
ATTAACTGGC GAACTACTTA CTCTAGCTTC CCGGCAACAA TTAATAGACT 1000
GGATGGAGGC GGATAAAGTT GCAGGACCAC TTCTGCGCTC GGCCCTTCCG 1050
GCTGGCTGGT TTATTCGTGA TAAATCTGGA GCCGGTGAGC GTGGGTCTCG 1100
CGGTATCATT GCAGCACTGG GGCCAGATGG TAAGCCCTCC CGTATCGTAG 1150
TTATCTACAC GACGGGGAGT CAGGCAACTA TGGATGAACG AAATAGACAG 1200
ATCGCTGAGA TAGGTGCCTC ACTGATTAAG CATTGGTAAC TGTCAGACCA 1250
AGTTTACTCA TATATACTTT AGA                              1273
```

FIGURE 7

Lpp
ATG AAA GCT ACT AAA CTG GTA CTG GGC GCG GTA ATC CTG GGT TCT
Met Lys Ala Thr Lys Leu Val Leu Gly Ala Val Ile Leu Gly Ser

ACT CTG CTG GCA GGT *TGC TCC AGC AAC GCT AAA ATC GAT CAG
Thr Leu Leu Ala Gly Cys Ser Ser Asn Ala Lys Ile Asp Gln

Linker
GGA ATT
Gly Ile

OmpA aa 46-159
AAC CCG TAT GTT GGC TTT GAA ATG GGT TAC GAC TGG TTA GGT CGT
Asn Pro Tyr Val Gly Phe Glu Met Gly Tyr Asp Trp Leu Gly Arg

ATG CCG TAC AAA GGC AGC GTT GAA AAC GGT GCA TAC AAA GCT CAG
Met Pro Tyr Lys Gly Ser Val Glu Asn Gly Ala Tyr Lys Ala Gln

GGC GTT CAA CTG ACC GCT AAA CTG GGT TAC CCA ATC ACT GAC GAC
Gly Val Gln Leu Thr Ala Lys Leu Gly Tyr Pro Ile Thr Asp Asp

CTG GAC ATC TAC ACT CGT CTG GGT GGC ATG GTA TGG CGT GCA GAC
Leu Asp Ile Tyr Thr Arg Leu Gly Gly Met Val Trp Arg Ala Asp

ACT AAA TCC AAC GTT TAT GGT AAA AAC CAC GAC ACC GGC GTT TCT
Thr Lys Ser Asn Val Tyr Gly Lys Asn His Asp Thr Gly Val Ser

CCG GTC TTC GCT GGC GGT GTT GAG TAC GCG ATC ACT CCT GAA ATC
Pro Val Phe Ala Gly Gly Val Glu Tyr Ala Ile Thr Pro Glu Ile

GCT ACC CGT CTG GAA TAC CAG TGG ACC AAC AAC ATC GGT GAC GCA
Ala Thr Arg Leu Glu Tyr Gln Trp Thr Asn Asn Ile Gly Asp Ala

CAC ACC ATC GGC ACT CGT CCG GAC AAC
His Thr Ile Gly Thr Arg Pro Asp Asn

Linker
GGA ATT CCG GGT
Gly Ile Pro Gly

ß-lactamase
CAC CCA GAA ACG CTG GTG AAA GTA AAA GAT GCT GAA GAT CAG TTG
His Pro Glu Thr Leu Val Lys Val Lys Asp Ala Glu Asp Gln Leu GGT GCA CGA GTG GGT TAC ATC GAA CTG GAT CTC AAC AGC GGT AAG
Gly Ala Arg Val Gly Tyr Ile Glu Leu Asp Leu Asn Ser Gly Lys ATC CTT GAG AGT TTT CGC CCC GAA GAA CGT TTT CCA ATG ATG AGC
Ile Leu Glu Ser Phe Arg Pro Glu Glu Arg Phe Pro Met Met Ser ACT TTT AAA GTT CTG CTA TGT GGC GCG GTA TTA TCC CGT GTT GAC
Thr Phe Lys Val Leu Leu Cys Gly Ala Val Leu Ser Arg Val Asp

FIGURE 8

```
GCC GGG CAA GAG CAA CTC GGT CGC CGC ATA CAC TAT TCT CAG AAT
Ala Gly Gln Glu Gln Leu Gly Arg Arg Ile His Tyr Ser Gln Asn

GAC TTG GTT GAG TAC TCA CCA GTC ACA GAA AAG CAT CTT ACG GAT
Asp Leu Val Glu Tyr Ser Pro Val Thr Glu Lys His Leu Thr Asp

GGC ATG ACA GTA AGA GAA TTA TGC AGT GCT GCC ATA ACC ATG AGT
Gly Met Thr Val Arg Glu Leu Cys Ser Ala Ala Ile Thr Met Ser

GAT AAC ACT GCG GCC AAC TTA CTT CTG ACA ACG ATC GGA GGA CCG
Asp Asn Thr Ala Ala Asn Leu Leu Leu Thr Thr Ile Gly Gly Pro

AAG GAG CTA ACC GCT TTT TTG CAC AAC ATG GGG GAT CAT GTA ACT
Lys Glu Leu Thr Ala Phe Leu His Asn Met Gly Asp His Val Thr

CGC CTT GAT CGT TGG GAA CCG GAG CTG AAT GAA GCC ATA CCA AAC
Arg Leu Asp Arg Trp Glu Pro Glu Leu Asn Glu Ala Ile Pro Asn

GAC GAG CGT GAC ACC ACG ATG CCT GCA GCA ATG GCA ACA ACG TTG
Asp Glu Arg Asp Thr Thr Met Pro Ala Ala Met Ala Thr Thr Leu

CGC AAA CTA TTA ACT GGC GAA CTA CTT ACT CTA GCT TCC CGG CAA
Arg Lys Leu Leu Thr Gly Glu Leu Leu Thr Leu Ala Ser Arg Gln

CAA TTA ATA GAC TGG ATG GAG GCG GAT AAA GTT GCA GGA CCA CTT
Gln Leu Ile Asp Trp Met Glu Ala Asp Lys Val Ala Gly Pro Leu

CTG CGC TCG GCC CTT CCG GCT GGC TGG TTT ATT CGT GAT AAA TCT
Leu Arg Ser Ala Leu Pro Ala Gly Trp Phe Ile Arg Asp Lys Ser

GGA GCC GGT GAG CGT GGG TCT CGC GGT ATC ATT GCA GCA CTG GGG
Gly Ala Gly Glu Arg Gly Ser Arg Gly Ile Ile Ala Ala Leu Gly

CCA GAT GGT AAG CCC TCC CGT ATC GTA GTT ATC TAC ACG ACG GGG
Pro Asp Gly Lys Pro Ser Arg Ile Val Val Ile Tyr Thr Thr Gly

AGT CAG GCA ACT ATG GAT GAA CGA AAT AGA CAG ATC GCT GAG ATA
Ser Gln Ala Thr Met Asp Glu Arg Asn Arg Gln Ile Ala Glu Ile

GGT GCC TCA CTG ATT AAG CAT TGG*TAA CTG TCA GAC CAA GTT TAC
Gly Ala Ser Leu Ile Lys His Trp

TCA TAT ATA CTT TAG A
```

FIGURE 8 (CONT.)

EXPRESSION OF PROTEINS ON BACTERIAL SURFACE

The United States Government may have certain rights in the present invention pursuant to Grant No. BCS-9013007 awarded by the National Science Foundation.

BACKGROUND OF THE INVENTION

1. Field of the Invention

The invention relates generally to the exportation and localization of polypeptides to the external membrane surface of a gram-negative cell, to recombinant vectors useful for the transformation of a host cell and to chimeric genes that provide outer membrane targeting and transmembrane sequences. Methods are disclosed providing for surface expression of proteins, including antigenically active proteins, specific binding proteins and enzymatically active species.

2. Description of Related Art

There is substantial interest in the expression of selected proteins on the surface of bacteria. Many potential applications exist, including the production of genetically engineered whole cell adsorbents, construction of "peptide libraries" where bacteria carry different exposed sequences, cell-bound enzymes (another form of immobilization), and use as live vaccines or immunogens to generate antibodies.

One approach to obtaining surface expressed foreign proteins has been to use a native membrane protein as a carrier for a foreign protein. LamB, an outer membrane protein of *Escherichia coli*, has been fused with peptides varying in length up to about 60 amino acids with successful expression of the hybrid protein at a recombinant host cell surface (Charbit, et al., 1991). Unfortunately, only relatively short polypeptides are surface-expressed using this method. Outer membrane proteins have "loop" regions spanning the membrane surface and while it is possible to substitute foreign DNA into the gene regions encoding the loop regions, there are only a limited number of insertions possible, constrained by the size of the loop region and, apparently, by the requirement to preserve the penetration and translocating properties of the membrane protein.

In general, attempts to develop methods of anchoring larger proteins as well as the smaller peptides on a bacterial cell surface have focused on fusion of the desired recombinant polypeptide to a native protein that is normally exposed on the cell's exterior in hope that the resulting hybrid will also be localized on the surface. The problem with this approach is that fusion of the foreign protein interferes with localization and, in many cases, the hybrid molecule is unable to reach the cell surface.

Nevertheless, in one example employing the Klebsiella enzyme pullulanase, a normally periplasmic protein, β-lactamase, was translocated through the *E. coli* outer membrane. C-terminal regions of pullulanase were replaced with DNA segments encoding β-lactamase or alkaline phosphatase. Only the hybrid protein with β-lactamase was transported to the cell surface (Kornacker and Pugsley, 1990). However, the surface-expressed protein was only transiently anchored to the cell surface, suggesting a severe limitation on the potential value of any other proteins expressed by this method as surface immunogens, adsorbents, or surface immobilized species. Furthermore, the assembly of pullulanase fusions onto the cell surface is a very complicated process requiring the presence of at least 14 foreign gene products in the host cell. It should be noted that alkaline phosphatase fused to the same pullulanase sequence could not be localized on the cell surface (Kornacker and Pugsley 1990).

The mechanisms of protein insertion within- and translocation across- the outer membrane of gram-negative bacteria are not well understood. For some outer membrane proteins, such as the PhoE porin, the information necessary for proper localization and assembly is interspersed within the primary sequence (Bosch et al., 1986; Bosch et al., 1989). Alternatively, the targeting signal may be contained within a single short continuous segment. For example, the first nine N-terminal amino acids of the major *E. coli* lipoprotein are necessary for proper localization in the outer membrane. Fusion to this short sequence is sufficient to direct the normally soluble periplasmic protein β-lactamase to the outer membrane (Ghrayeb and Inouye, 1984). Similarly, extensive studies with OmpA have suggested that the region between residues 154 and 180 is crucial for localization (Klose et al., 1988a, 1988b). With OmpA, targeting and outer membrane assembly appear to be distinct events. Only large fragments containing the entire membrane spanning sequence of OmpA are able to assemble into a conformation exhibiting native resistance to proteolytic digestion (Klose et al., 1988a).

In general, amino acid substitutions or insertions within outer membrane loops exposed on the cell surface are well tolerated and do not interfere with the folding of the protein in the membrane. Peptides as large as 60 amino acids have been inserted within external loops of various outer membrane proteins and appear to be exposed on the surface of intact *E. coli* cells as indicated by immunochemical techniques (Charbit et al., 1991). However, efforts to direct soluble reporter proteins such as alkaline phosphatase, to the cell surface using outer membrane protein fragments have not been successful. These fusions either end up at incorrect cellular locations or become anchored in the membrane with the secreted protein domain facing the periplasm (Murphy et al., 1990). In gram-negative bacteria the outer membrane acts as a barrier to restrict the export of proteins from the cell. Normally only pilins, flagellins, specific enzymes and a few toxins are completely transported across the outer membrane (Kornacker and Pugsley, 1990). Most of these proteins are first secreted into the periplasmic space via the general secretion pathway and then cross the outer membrane by a process that involves the action of several additional gene products (Filloux et al., 1990).

Whole cell adsorbents are considered to have potential value for biotechnology applications for the purification of various molecules or the selective removal of hazardous compounds from contaminated waste waters. However, a major constraint in the development of whole cell adsorbents is the availability of bacterial strains with suitable ligands on their surface. Although functional antibody fragments have been produced in *Escherichia coli* (Skerra and Pluckthun 1988, Better et al. 1988, Orlandi et al. 1989, Sastry et al. 1989), these polypeptides have not been expressed on the cell surface. Indeed, a "library" of recombinant immunoglobulins containing both heavy and light variable domains (Huse et al. 1989) has been produced with the proteins having antigen-binding affinity comparable to the corresponding natural antibodies. Furthermore, the variety of recombinant immunoglobulins from bacteria is greater than the number of antibody molecules that can be generated by the mammalian cell. In this way it has become possible to expand the repertoire of antibodies that can be made by the immune system (Huse et al. 1989). While the availability of such a wide range of immunoglobulins suggests the potential for creation of E. coli cells endowed with immunological surface receptors, there has been little success in producing recombinant proteins on the surface of bacterial cells, and conspicuous lack of a method to generate recombinant immunoglobulins on surfaces of gram negative host cells.

Although the potential repertoire of immunoglobulins produced in an immunized animal is high ($>10^{10}$), only a small number of monoclonal antibodies can be generated using hybridomas. This limitation complicates the isolation of antibodies with specific properties, such as the ability to act as a catalyst. Combinational antibody libraries comprising millions of genes of different antibodies have been cloned using phage λ(Huse et al., 1989). However, screening the library to select the desired clone can be extremely time consuming and complicated. One approach to the screening problem has been an attempt to express antibodies on the surface of filamentous phage. Phage particles displaying high affinity antibody molecules on their surface can be enriched by chromatography through a column of immobilized antigen (Barbas et al., 1991; Clarckson et al., 1991; Breitling, 1991). Although the feasibility of this technique has been demonstrated, several problems are apparent, including: (1) fusion to bacteriophage coat proteins causing interference with antibody folding, (2) subcloning of large numbers of positive phage particles in order to produce soluble antibody fragments to carry out more extensive characterization, and (3) lack of control of the number of antibody molecules on the phage surface, thus affecting binding to the immobilized antigen and complicating the selection procedure.

SUMMARY OF THE INVENTION

The present invention addresses one or more of the foregoing problems in providing a versatile recombinant vector that will promote transport of a periplasmic or other protein to the external face of the outer membrane of a gram-negative bacterial cell in the absence of any specific export components. In particular, the vector includes a tripartite chimeric gene having a membrane targeting sequence, a membrane translocating sequence capable of locating a fusion protein on the outer surface and a gene segment encoding any of a variety of proteins.

Overall and in general the tripartite chimeric genes of the invention include at least three DNA segments. One segment is a targeting DNA sequence encoding a polypeptide capable of targeting and anchoring the fusion polypeptide to a host cell outer membrane. Targeting sequences are well known and have been identified in several of membrane proteins including Lpp. Generally, as in the case of Lpp, the protein domains serving as localization signals are relatively short. The Lpp targeting sequence includes the signal sequence and the first 9 amino acids of the mature protein. These amino acids are found at the amino terminus of Lpp. E. coli outer membrane lipoproteins from which targeting sequences may be derived include TraT, OsmB, NlpB and BlaZ. Lipoprotein 1 from Pseudomonas aeruginosa or the PA1 and PCN proteins from Haemophilus influenza as well as the 17 kDa lipoprotein from Rickettsia rickettsii and the H.8 protein from Neisseria gonorrhea and the like may be used.

A second component of tripartite chimeric genes is a DNA segment encoding a membrane-transversing amino acid sequence. Transversing is intended to denote an amino acid sequence capable of transporting a heterologous or homologous polypeptide through the outer membrane. In preferred embodiments, the membrane transversing sequence will direct the fusion polypeptide to the external surface. As with targeting DNA segments, transmembrane segments are typically found in outer membrane proteins of all species of gram-negative bacteria. Transmembrane proteins, however, serve a different function from that of targeting sequences and generally include amino acids sequences longer than the polypeptide sequences effective in targeting proteins to the bacterial outer membrane. For example, amino acids 46–159 of the E. coli outer membrane protein OmpA effectively localize a fused polypeptide to the external surface of the outer membrane when also fused to a membrane targeting sequence. These surface exposed polypeptides are not limited to relatively short amino acid sequences as when they are incorporated into the loop regions of a complete transmembrane lipoprotein. While the invention has been demonstrated with a transmembrane directing protein sequence from OmpA, other transmembrane directing sequences from outer membrane proteins may be employed.

The third gene segment comprising the tripartite chimeric gene fusion is a DNA segment that encodes any one of a variety of desired polypeptides. This DNA segment is positioned downstream from the DNA segment encoding the transmembrane sequence. The tripartite chimeric gene when provided with a functional promoter is expressible in gram-negative host cells.

A particular embodiment of the invention includes recombinant vectors prepared from the hereindescribed tripartite chimeric gene fusions. Such vectors will express fusion polypeptides at the outer membrane cell surface of a gram-negative host cell. These recombinant vectors include a functional promoter sequence and a targeting DNA sequence encoding a protein capable of targeting to the outer surface of a gram-negative bacterial host cell. The targeting gene is typically positioned downstream of the promoter sequence. A transmembrane gene sequence is positioned downstream of the targeting gene sequence. The transmembrane sequence will encode a protein domain capable of transversing the cell outer membrane. The vector will also include a DNA sequence which encodes a desired protein. This sequence when positioned downstream of the transmembrane sequence will be expressed on the external surface of the outer membrane, and typically is exposed to the external medium while remaining stably anchored to the membrane surface.

A most preferred embodiment of the recombinant vector is plasmid pTX101. This plasmid contains a fusion of the signal sequence and the first 9 amino acids of the major outer membrane lipoprotein of E. coli, a 342-base pair fragment from the outer membrane protein OmpA and the coding sequence for the complete mature β-lactamase protein. However, clearly numerous variations of the disclosed recombinant vectors could be prepared using techniques well known to those of skill in the art. DNA sequences encoding regions from a wide variety of membrane proteins could be employed. Such regions may be fused with any of a number of genes or gene fragments via a polylinker region.

The polypeptides encoded by the nucleic acid segments identified herein have been described in terms of function related to targeting and transversing fusion polypeptides to a gram-negative bacterial cell outer membrane surface. The invention is intended to include variations of the fused genes disclosed to the extent that the encoded polypeptides are functionally biologically equivalent. In general, by biologically functionally equivalent is meant amino acid sequences that may vary from certain of the disclosed fusion products, by e.g., natural genetic drift, strain or subspecies antigenic variation or by mutation of the DNA molecules without loss of appropriate membrane targeting or transversing functions as described.

Likewise, certain changes in nucleic acid composition of genes encoding polypeptides having the aforementioned functions, will not affect the general broad concept of the invention. For example, vectors containing variant codons for a particular amino acid, while altering the DNA composition, will not change the amino acid identity. Minor base pair changes, while producing some variation in primary amino acid sequence of the encoded polypeptide, are not expected to substantially alter function. All such variations, whether in amino acid or nucleic acid composition, are contemplated to be within the scope of the invention.

The methods illustrated for the expression of desired recombinant polypeptides on the cell surface may also be achieved by fusion to protein domains other than those derived from the major lipoprotein and OmpA, provided that these domains can function for the expression of the desired polypeptide on the cell surface. Generally, the desired polypeptide is fused to an amino acid sequence that includes the signals for localization to the outer membrane and for translocation across the outer membrane. The amino acid sequences responsible for localization and for translocation across the outer membrane may be derived either from the same bacterial protein or from different proteins of the same or different bacterial species. Examples of proteins that may serve as sources of localization signal domains include *E. coli* outer membrane lipoproteins from such as TraT, OsmB, NlpB, BlaZ, *Pseudomonas aeruginosa* lipoprotein 1, *Haemophilus influenza* PA1 and PCN proteins, *Rickettsia rickettsii* 17 kDa lipoprotein, *Neisseria gonorrhea* H.8 protein and the like. A sequence that spans the outer membrane and serves to transport the desired recombinant polypeptide to the cell surface can be derived from a membrane spanning domain of suitable length from any native outer membrane protein of gram-negative bacteria, including the porins LamB, PhoE, OmpC and OmpF, as well as other outer membrane proteins such as OmpT, FepA, and the like.

Any of a wide variety of gram-negative bacteria may be useful in practicing the invention. Such gram-negative bacteria include *E. coli*, Salmonella, Klebsiella, Erwinia, and the like. *E. coli* and Salmonella are particularly preferred as host cells. Although there are variations among the bacteria outer membrane proteins are similar. Target and transversing sequences from any of the membrane proteins may be used in constructing vectors useful for exportation across the cell wall of gram-negative bacteria.

Another aspect of the invention includes transformants. A typical transformant is a Salmonella prepared by transformation with the described recombinant vectors. A most preferred transformant is *E. coli*.

The invention is typically practiced using one or more of the commonly available gram-negative bacteria as cell hosts. However, rough mutants having somewhat differing membrane compositions are expected to also be useful in the practice of the invention. Membranes with higher phospholipid content, for example, may for some fusion polypeptides, provide more efficient surface expression at higher temperatures. Alternatively, it may be desirable to anchor some polypeptides closer to the membrane surface with increased lipid-protein interactions, perhaps for the purpose of increasing immunogenic response or altering adsorbent properties. Such mutants, spontaneously generated or otherwise, are contemplated as useful as host cells and/or as sources for membrane directing and transversing sequences.

Numerous types of fusion polypeptides may be expressed using the aforementioned system. Relatively large proteins such as alkaline phosphatase have been expressed on the surface of *E. coli* host cells. In its dimeric form alkaline phosphatase has a molecular weight of greater than 80 kDa. Other large proteins are also expected to be effectively surface expressed. Examples of expressed polypeptides include $\beta$-lactamase, alkaline phosphatase, cellulose binding domain of cellulase, or single-chain $F_v$ antibody.

Expression of a variety of single-chain antibodies on the surface of a gram-negative bacterial host cell has several potential important applications particularly for the preparation of whole cell adsorbents. In addition, a variety of antigenic determinants may be expressed on a cell surface and used to prepare bacterial vaccines. A selected antigen in combination with an activating agent such as IL-4 on the surface of a bacterium may have potential use in stimulating an immune response toward a surface exposed antigen.

Tripartite chimeric gene fusions or the recombinant vectors herein described will typically include appropriate promoters. Such promoters are well known to those of skill in the art and examples include lpp promoter or lac promoter. Additionally, recombinant vectors also include a signal peptide. In preferred embodiments the signal peptide is positioned upstream of the targeting gene segment in recombinant vectors.

The invention also includes a method for expressing a fusion polypeptide anchored on the outer membrane surface of a gram-negative bacterial host cell. A gene segment encoding a desired polypeptide is selected and inserted by the herein described methods into one or more of the disclosed recombinant vectors. A selected gram-negative cell is transformed with the vector. The transformants are cultured and screened in order to identify clone transformants having a desired peptide expressed on the host cell surface. There are numerous ways the desired gene segment encoding the polypeptide could be incorporated into one or more of the disclosed recombinant vectors. For example, plasmid pTX101 may be cut with the restriction endonuclease EcoRI at the unique site in the linker region between the OmpA and $\beta$lactamase sequence. Typically, blunt ends are created on the DNA by treating with the Klenow fragment of DNA polymerase. Plasmids containing the coding sequence for the desired polypeptide may be isolated and DNA fragments obtained by cutting that plasmid with an appropriate endonuclease followed by blunt ending again using a Klenow fragment or similar polymerase. The linearized pTX101 vector and the desired gene fragment may then be ligated and the resultant DNA transformed into an appropriate bacterial host cell strain such as *E. coli* strain JM109.

Surprisingly, the temperature at which the cells are cultured has an effect on the expression of the desired polypeptide. Culturing at higher temperatures, about 40° C., for example, results in less efficient expression of the desired polypeptide on the surface of the bacterial host. Although expression on the surface may be obtained when culturing is performed between about 22°–40° C., a preferred temperature range is between 22°–27° C. and a most preferred temperature being around 24° C.

Yet another aspect of the present invention is a method for obtaining an immunogenic polypeptide. An immunogenic polypeptide to which it is desired to elicit an immune response is selected and then inserted into an appropriate recombinant vector prepared in accordance with the aforementioned procedures. Appropriate gram-negative cells are transformed and the culture screened for transformants. Transformants are then screened to determine the degree of immunogenicity and those that are highly immunogenic are used to obtain one or more antibodies. This method is particularly useful because it is known that surface expressed polypeptides typically elicit higher antigenic and immunogenic responses than those peptides that are not immobilized on a bacterial surface. Surface exposed immunogenic polypeptides may also be used to prepare vaccines, typically by mixing the cells in a pharmaceutically acceptable vehicle suitable for administration in mammals.

Antibodies can be equally well expressed on the surface of the cell. When such antibodies are expressed on cell surfaces those with high affinity for particular antigens may be selected. Variants of antibodies may be prepared and surface expressed and antibody-like sequences may be prepared and tested for affinity to the appropriate antigens.

In yet another aspect of the invention it is contemplated that kits useful for transforming gram-negative bacterial host cells may be prepared. Kits will include at least one recombinant vector prepared in accordance with the herein described invention in an appropriately compartmentalized container. A preferred recombinant vector is defined by SEQ ID NO:1.

The invention also includes a method for removing contaminants from fluids. In this method various receptor proteins expressed on the outer membranes of gram-negative bacteria may be used to selectively interact with a wide variety of undesirable compounds. Metallothionein, for example, binds with a wide variety of heavy metals including iron, cadmium, zinc, copper, vanadium, and similar metals. When bound to the surface of a gram-negative organism this protein is expected to efficiently remove heavy metals from aqueous samples.

Whole cell adsorbents, with surface expressed polypeptides, such as selected antibodies, may be used to remove biological contaminants, for example, bacterial endotoxin from water samples. The efficiency of such whole cell adsorbents may be increased by cross-linking the bacterial surface. This also may increase the stabilization of the cells against disruption. One method of stabilization involves the specific cross-linking of the cells through the lipopolysaccharide component of the surface. Thus the cells can be aggregated and stabilized without affecting the function of surface-expressed proteins. Other types of cell adsorbents are contemplated including the use of cellulose binding domains, starch binding domains, protein A, lectins, or protease receptors expressed on outer membrane bacterial cell surfaces.

Still further embodiments of the invention include immobilized enzyme systems. Any one of a wide variety of biocatalytically active polypeptides may be expressed on the surface of a bacterial cell using the disclosed methods. Advantages of having an enzyme expressed on the bacterial cell surface include increased accessibility to substrates, stability, and potentially increased lipid solubility. In a more particular embodiment, biocatalytically active polypeptides immobilized on host cell membranes without additional bacterial host cell components may be used in biphasic reaction systems. Enhanced lipid solubility of the immobilized enzymes enables catalyst substrate interaction in the lipophilic solvents with extraction of the water soluble products into the aqueous phase. Further contemplated embodiments in such an immobilized system include encapsulating immobilized enzymes on membrane surfaces within liposomes or similar vesicles.

As part of the invention, kits useful for the expression of fusion proteins are also envisioned comprising a container having suitably aliquoted reagents for performing the foregoing methods. For example, the containers may include one or more vectors, examples being the vectors of claim 2, particular embodiments of which are shown schematically in FIG. 5. Suitable containers might be vials made of plastic or glass, various tubes such as test tubes, metal cylinders, ceramic cups or the like. Containers may be prepared with a wide range of suitable aliquots, depending on applications and on the scale of the preparation. Generally this will be an amount that is conveniently handled so as to minimize handling and subsequent volumetric manipulations. Most practitioners will prefer to select suitable nucleases such as EcoRI, BamHI, or PstI from common supplies usually on hand; however, such restriction endonucleases could also be optionally included in a kit preparation.

Vectors supplied in kit form are preferably supplied in lyophilized form, although such DNA fragments may also be taken up in a suitable solvent such as ethanol, glycols or the like and supplied as suspensions. For most applications, it would be desirable to remove the solvent which for ethanol, for example, is a relatively simple matter of evaporation.

BRIEF DESCRIPTION OF THE DRAWINGS

FIG. 3A: Samples from every three fractions were pooled together and loaded in consecutive lanes. Lanes 2-8, pTX109: lanes 9-15, pJG311. Lanes: 1: Molecular weight markers: 2: fractions 1-3; 3: fractions 4-6; 4: fractions 7-9; 5: fractions 10-12; 6: fractions 13-15; 7: fractions 16-18; 8: fractions 19-21; 9: fractions 1-3; 10: fractions 4-6;11: fractions 7-9; 12: fractions 10-12; 13: fractions 13-15; 14: fractions 16-18; 15: fractions 19-21; 16: molecular weight markers. The molecular weight standards (BRL) are: myosin H-chain, 200 kDa: phosphorylase B, 97 kDa: bovine serum albumin, 68 kDa: ovalbumin, 43 kDa: and carbonic anhydrase, 29 kDa. Arrows indicate the fusion proteins Lpp-OmpA-$\beta$-lactamase (lane 2) and Lpp-$\beta$-lactamase (lane 9). FIG. 3B: Western blot of the JM109(pTX101) fractions from the sucrose gradient (FIG. 3A, lanes 2-8). The primary antibody was used at a concentration of 1:20.000. The gel was overloaded to show the presence of degradation products. There were no degradation products below the 32.000 dalton molecular weight standard. As with the native $\beta$-lactamase, the Lpp-OmpA-$\beta$-lactamase migrates as two bands depending on the oxidation of the single disulfide bond (30). The prestained molecular weight markers (Bio-Rad) have apparent molecular weights of: 106 kDa, phosphorylase B: 80 kDa, bovine serum albumin: 49 kDa, ovalbumin: 32 kDa, bovine carbonic anhydrase.

FIG. 7 (SEQ ID NO:1) shows the DNA sequence of the genes coding for the tripartite fusion from pTX101.

FIG. 8 shows the condons for the segments included in the tripartite fusion from pTX101.

DETAILED DESCRIPTION OF THE PREFERRED EMBODIMENTS

Materials and Methods

Bacterial Strains

Figure 1:
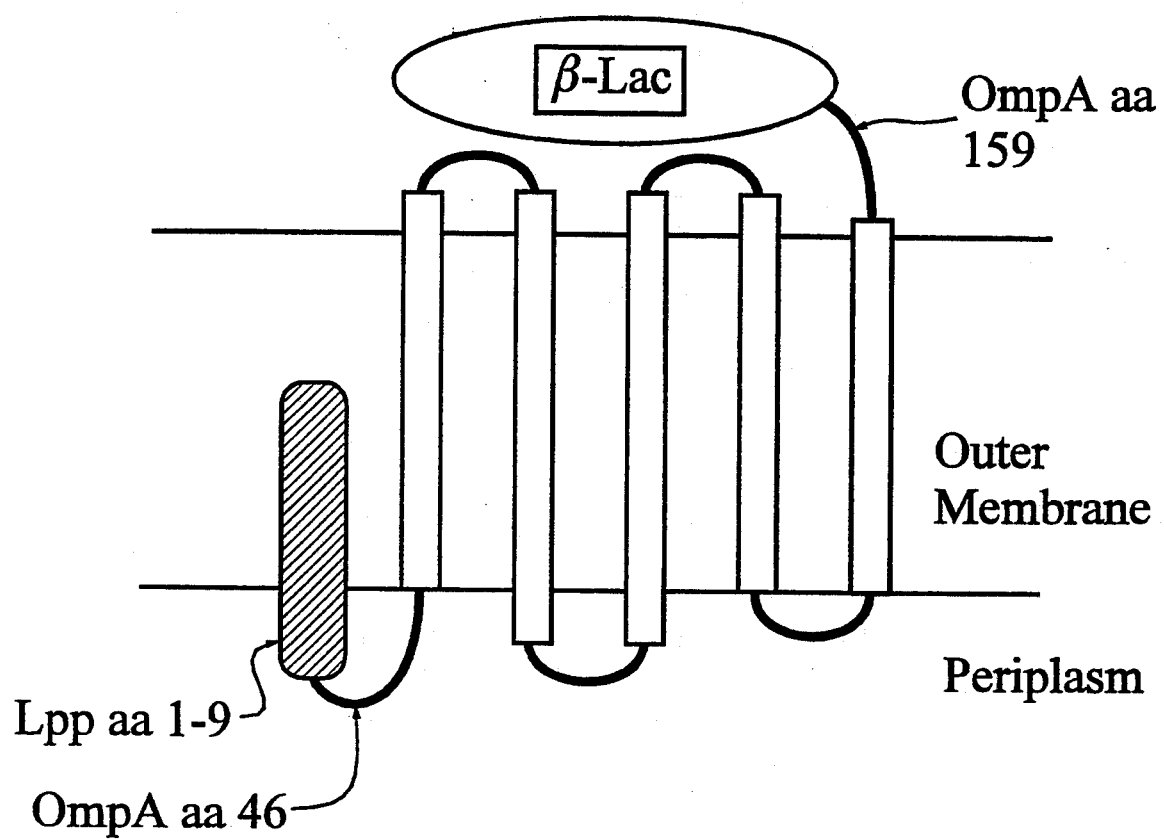
FIG. 1 is a schematic diagram of the Lpp-OmpA-$\beta$-lactamase fusion in the outer membrane of a gram negative bacterium. Rectangles represent membrane-spanning $\beta$-strands of OmpA.

E. coli strain JM109 (endA1 recA1 gyrA thi-1 hsdR17($r_k^-m_k^+$) relA1 supE44 X(lac-proAB) /F' traD36 proAB lacI$^q$ lacZΔM15) (Invitrogen, San Diego, Calif.), ATCC 53323.

Escherichia coli strain JCB572 is obtained from Dr. J. Beckwith, Department of Molecular Biology and Molecular Genetics, Harvard Medical School, Boston, Mass. 02115 (Bardwell et al., 1991).

Plasmids

Plasmid pSWFII is prepared as described by Ehrmann et al., 1990.

Plasmid pJG311 (Ghrayeb and Inouye, 1984; Yamaguchi et al., 1988) was constructed by cutting pMH014 Cm$^r$ (Yamaguchi et al., 1988) which contains the gene coding for the signal sequence and mature major outer membrane lipoprotein, with EcoRI and then removing all the lipoprotein gene except the signal sequence and the first nine amino acids. The $\beta$-lactamase gene, cut from pTG206, was ligated into this site creating pJG202. The region coding for the lipoprotein signal sequence, the first nine amino acids from the lipoprotein, and the entire mature $\beta$-lactamase, was transferred from pJG202 to the expression plasmid pIN-III-A-Cm$^r$ (Yoshihiro et al., 1983) to create pJG311, which contains a Lpp-$\beta$-lactamase fusion. Plasmid pJG311 may also be obtained from Masayori Inouye, Department of Biochemistry, Robert Wood Johnson Medical at Rutgers University of Medicine and Dentistry of New Jersey, Piscataway, N.J. USA 08854.

Plasmid pRD87 is constructed in the same manner as pTU500 (Freudl et al., 1985). pTU500 is constructed by cutting the OmpA gene from pTU500/1 and ligating it into pUC9 (Vieira and Messing, 1982) thereby placing it under the control of the lac promoter. pRD87 was made identically except that the ompA gene from pTU500/1 was cloned into pUC8 (Vieira and Messing, 1982). The two plasmids, pTU500 and pRD87, are identical except that pTU500 contains an amber mutation at the seventh codon in the ompA sequence, while pRD87 does not contain the amber mutation. Plasmid pRD87 may also be obtained from Ulf Henning, Max-Planck-Institut fur Biologie, Corrensstrasse 38, D-7400 Tübingen, Germany.

Cultures

Cultures were grown in either LB medium (Difco) supplemented with 0.2% glucose or M9 medium supplemented with 0.2% casein amino acid hydrolysate and 0.2% glucose. The desired antibiotics were added as required.

General Procedures

SDS-PAGE was performed on 11% and 15% acrylamide gels. Protein samples, denatured for 5 minutes in boiling SDS containing $\beta$-mercaptoethanol, were loaded onto polyacrylamide gels and run at a constant current. The gels were stained with Coomassie brilliant blue (R 250) for 15 minutes and the background stain was removed overnight with a methanol/acetic acid destaining solution.

Western blots were performed by running 0.5 μg protein samples on polyacrylamide gels at constant current and were transferred overnight to nitrocellulose membranes. The membranes were incubated for 1 hour with rabbit anti-$\beta$-lactamase antibodies, rinsed, and incubated for 1 hour with horseradish peroxidase conjugated goat anti-rabbit antibodies. After further rinsing, the membranes were developed with 4-chloro-1-naphthol, which gives a distinct blue color at the sites containing horseradish peroxidase.

The enzymatic activity of $\beta$-lactamase was measured by the rate of hydrolysis of penicillin G or nitrocefin (Samuni, 1975; O'Callaghan et al., 1972). Hydrolysis of penicillin G gives linear decrease in the adsorption of light at 240 nm, while nitrocefin hydrolysis shows an adsorption increase at 482 nm. The changes in adsorption with time were measured in an LKB spectrophotometer. Protein concentrations were measured by the Bio-Rad assay using standard curves prepared from protein standards and comparing color developed with the reagent measured at 595 nm in a spectrophotometer.

The present invention relates to a novel chimeric gene from which a wide variety of recombinant expression vectors useful for surface expression of desired proteins is possible. Appropriately transformed gram-negative host cells will efficiently express proteins on the outer membrane surface without loss of inherent activity. A novel aspect of the fused gene is the use of three separate DNA segments which act respectively (1) to target a fusion product to the host cell outer membrane and (2) to transverse the fusion product across the membrane to the outer surface where (3) the polypeptide expressed by a fused gene of interest becomes stably anchored to the surface.

The particular examples herein illustrated utilize recombinant vectors constructed from known DNA segments having particular functions. For example, various membrane proteins such as OmpA are known to contain both membrane targeting and transversing sequences. However, fusion of alkaline phosphatase with outer membrane proteins has not produced surface expressed alkaline phosphatase (Murphy et al., 1990). The present invention utilizes separate targeting and transversing domains. When engineered into a vector such that a gene for a desired polypeptide product is positioned downstream of both the targeting and transversing sequences, efficient surface expression of the product is effected. Moreover, the targeting sequence is positioned upstream of the transversing sequence.

Figure 6:
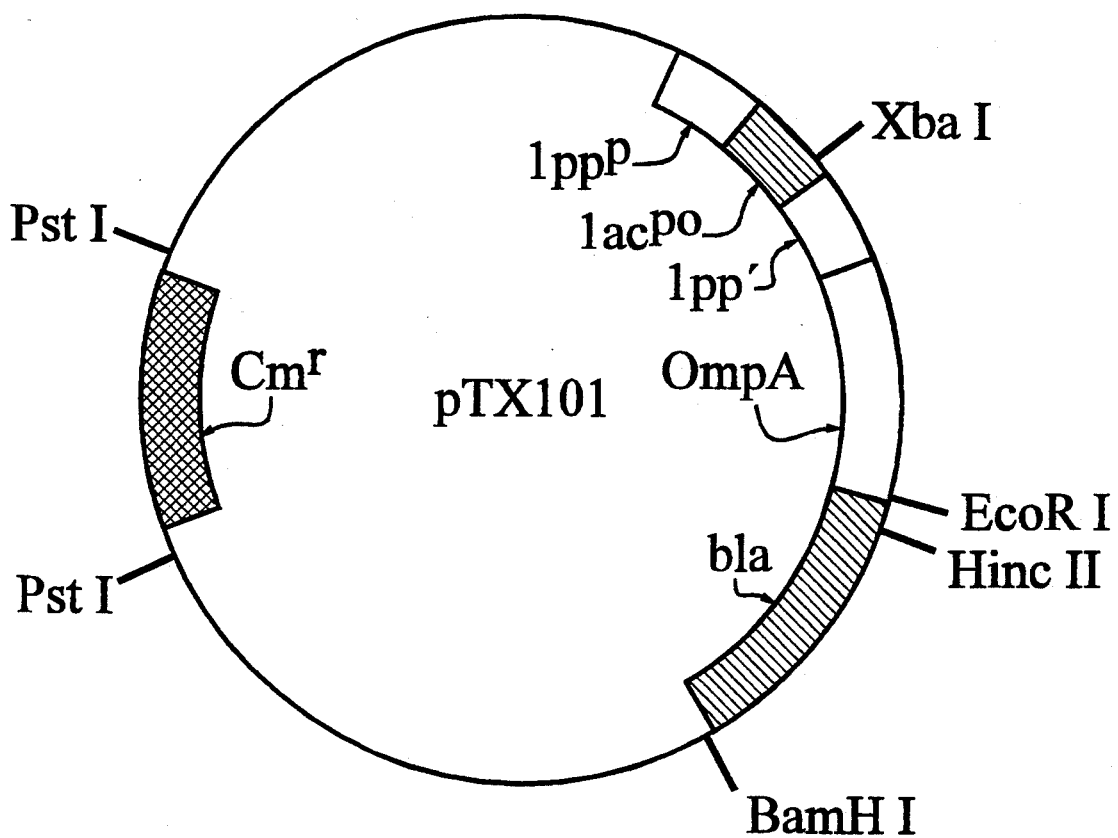
FIG. 6 shows a diagram of the plasmid pTX101.

It will be appreciated that the particular gene sequences shown here to construct a tripartite chimeric gene are not limited to deriving targeting and transversing sequences from lipoprotein and OmpA respectively. Other sequences with analogous function may be used. In particular, this invention may be efficiently practiced with the construct shown schematically in FIG. 6 and in particular detail in FIG. 7 (SEQ ID NO:1) illustrates useful targeting and transversing DNA sequences fused with the β-lactamase gene, although it is appreciated that numerous other polypeptide sequences could be used rather than β-lactamase.

The invention has numerous applications, a brief background for which is described.

Whole Cell Affinity Adsorbents

Affinity purifications of biomolecules rely primarily on the strong interactions between proteins and ligands. Typically, the ligand is bound to a solid support matrix which is employed in a chromatographic-type separation. More recently, suspensions of starch granules (Mattiasson and Ling 1986) or liposomes (Powell et al. 1989) have been used as supports for affinity purifications. In some of the most useful and specific separations, the affinity ligands are proteins such as antibodies, lectins or protein receptors (Mohr and Pommerening 1986, Turkova 1978). The preparation of protein affinity adsorbents involves the production, purification and the immobilization of the polypeptide on a solid support matrix. These three steps are generally complicated and often prohibitively expensive for large scale applications. On the other hand bacterial cells expressing proteins on their surface can serve as an important source of low cost solid phase adsorbents.

The human metallothionein gene protein has been expressed as a fusion with an outer membrane protein (Jacobs et al., 1989). Because of the way the fusion protein was constructed, metallothionein was localized on the internal side of the E. coli outer membrane, i.e., facing the periplasmic space. Nevertheless, since metal ions can diffuse through the outer membrane, the recombinant cells were able to bind as much as 66 fold more $Cd^{+2}$ than normal E. coli. Another example of a high affinity cellular adsorbents (e.g., Kronvall et al. 1979) includes the use of cultured mammalian cells to remove viral impurities from blood samples (Tsao et al., 1988).

Whole Cells As Enzyme Carriers For Bioprocessing

The use of whole cells as enzymatic catalysts has been in use for several years. Typically, a microorganism which produces a certain enzyme is used as a biocatalyst, thus avoiding the costs associated with protein purification and immobilization steps. Usually the cells are first killed, treated with a permeabilizing agent to allow the diffusion of reactants and products into the cytoplasm and finally they are stabilized using some form of chemical crosslinking (Tampion and Tampion 1987). Several improvements on the preparation of whole cell biocatalyst have been made over the years. However, certain inherent limitations can not be overcome with the currently available technology. These are: i) The chemical methods which are used for permeabilization of the cell membrane can also result in deactivation of the important enzyme; ii) Other intracellular enzymes may compete for the reaction substrate giving rise to undesired byproducts and decreased yields; and iii) Intracellular degradation processes can limit the functional life of the biocatalyst. Clearly, all these problems can be eliminated if the enzyme is attached to the cell's exterior.

Live Bacterial Vaccines

Genetically weakened (attenuated) strains of bacteria that are able to survive and persist in the human or animal body can confer prolonged immunological protection against disease (Stover 1991). Non-recombinant live vaccines have been used for many years for large scale vaccinations (Dougan 1989). For example, live attenuated cultures of Baccillus Calmette-Guérin (BCG) which confer immunity against tuberculosis represent the most widely used vaccine in the world (Stover et al. 1991). Recently, emphasis has been shifted to the development of recombinant bacterial vaccines (Curtiss et al. 1989, Charles and Dougan 1990). In this case vaccination consists of the oral administration of a live culture of an attenuated enteric bacterium host such as E. coli or Salmonella typhimurium which expresses an antigenic peptide from a pathogen. Within the body, some of the bacteria find their way to the intestinal tract where they coexist with the wild type E. coli and other enteric microorganisms. In this way they ensure the presence of a low level of antigenic peptide in the body. Live vaccines provide more efficient immunity and longer protection against infections compared to subunit or killed bacterial vaccines. There are several reasons for the higher efficacy of live bacterial vaccines (Dougan et al. 1989): i) Protection correlates with how long the vaccine is present in the body (De Libero and Kaufman, 1986). Since the bacteria persist in the intestine for very long times, they are able to confer extended immunity; ii) Unlike most currently used vaccines, bacterial vaccines may be administered orally; and iii) Several antigens may be expressed simultaneously in bacteria thus giving rise to multipurpose vaccines.

Although the foregoing antigen may stimulate an immune response even when produced within the cell, the immunogenicity of peptide antigens can be greatly enhanced if they are expressed on the surface of an appropriate host strain (Taylor et al. 1990). This is because the surface of the bacteria such as Salmonella or E. coli acts as an adjuvant to enhance the immune response to the antigen. The most straightforward way to accomplish this is to insert the foreign peptide within a surface exposed loop of an outer membrane protein which serves as the targeting signal. A fusion protein with the structure outer membrane protein--peptide--outer membrane protein is constructed and then the normal protein localization mechanism of the cell is exploited to carry the peptide to the surface. There appears, however to be an upper limit on the length of foreign polypeptides that can be inserted within outer membrane proteins. The maximum size of foreign sequence that can be accommodated within outer membrane proteins is around 45 to 50 amino acids (Newton et al. 1989, Charbit et al. 1988).

Several different outer membrane proteins have been exploited as targeting vehicles for the localization of foreign peptides (e.g., Charbit et al., 1988). A number of short amino acid sequences have been inserted within a surface exposed loop of the *E. coli* outer membrane protein maltoporin (LamB) (Charbit et al., 1988). The peptides were localized correctly so that the whole cells could be used to induce an immune response. Expression systems for the localization of antigenic peptides on bacterial surfaces have also been constructed using the *E. coli* K88ac and K88ad pilin proteins (Thiry et al. 1989), the *S. typhimurium* flagellin, (Newton et al. 1989) the TraT lipoprotein (Taylor et al. 1990) and the *E. coli* outer membrane porins PhoE, OmpA and OmpC (Agterberg 1987, Freundl 1989).

Prototype live bacterial vaccines have been prepared using cells having sequences from the influenza virus, cholera toxin B subunit and the gp 120 glycoprotein of HIV-1 expressed on their surface. However, the presence of a fragment of a protein from an infectious agent often does not give satisfactory protection against disease (Dougan et al. 1989).

An advantage of the present invention is the potential to express complete proteins from infectious agents on the surface of the carrier cells. Immunization with an intact protein is more likely to elicit a humoral immune response and provide protective immunity.

Vaccine Preparation and Use

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

Live bacterial vaccines are conventionally administered parenterally, by injection or in oral formulation. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

In many instances, it will be desirable to have multiple administrations of the vaccine, usually not exceeding six vaccinations, more usually not exceeding four vaccinations and preferably one or more, usually at least about three vaccinations. The vaccinations will normally be from two to twelve week intervals, more usually from three to five week intervals. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

The invention also contemplates the use of disclosed nucleic acid segments in the construction of expression vectors or plasmids and use in host cells. The following is a general discussion relating to such use and the particular considerations in practicing this aspect of the invention.

Host Cell Cultures and Vectors

In general, of course, prokaryotes are preferred for the initial cloning of DNA sequences and constructing the vectors useful in the invention. For example, in addition to the particular strains mentioned in the more specific disclosure below, one may mention by way of example, strains such as *E. coli* K12 strain 294 (ATCC No. 31446), *E. coli* B, and *E. coli* X 1776 (ATCC No. 31537). These examples are, of course, intended to be illustrative rather than limiting.

Prokaryotes are also preferred for expression. The aforementioned strains, as well as *E. coli* W3110 (F-, lambda-, prototrophic, ATCC No. 273325) or other enterobacteriaceae such as *Salmonella typhimurium* or *Serratia marcesans*, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells.

For example, E. coli is typically transformed using pBR322, a plasmid derived from an E. coli species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the microorganism for expression.

Those promoters most commonly used in recombinant DNA construction include the lactose promoter systems (Chang et al., 1978; Itakura et al., 1977; Goeddel et al., 1979) and a tryptophan (trp) promoter system (Goeddel et al., 1979; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in E. coli from their own promoter sequences, precluding the need for addition of another promoter by artificial means.

The following examples are intended to illustrate the practice of the present invention and are not intended to be limiting. Although the invention is here demonstrated with βlactamase expressed on the surface of a cell membrane, numerous other proteins with various functions could be similarly expressed. These would include polypeptides with catalytic functions, metal binding capability and specific binding activity toward cell receptor sites. Moreover, the expression vectors and chimeric genes used therein may be constructed from a wide variety of targeting and transversing sequences, and are not limited to those derived from OmpA and Lpp.

EXAMPLE 1

The following example illustrates the construction of a recombinant vector encoding a desired protein, targeting and membrane translocating sequences. When used to transform suitable bacterial hosts, such a vector enables surface expression of active proteins, as shown here for the production of β-lactamase.

Construction of Plasmid pTX101 Containing Tripartite Chimeric Gene for β-Lactamase Expression Plasmid pTX101 was prepared from pJG311, which contains the signal sequence and first 9 N-terminal amino acids of the mature major outer membrane lipoprotein of E. coli and the complete β-lactamase sequence. A unique EcoRI site in the linker region between the peptide region and the β-lactamase was cut with EcoRI. The cut plasmid was isolated from a low melting point agarose gel and the ends were made blunt using the Klenow fragment. pRD87, containing the OmpA gene, was simultaneously cut with HpaI and SphI, both unique sites, generating a 342 bp fragment containing the sequence for five of the eight outer membrane spanning domains of OmpA. This fragment was isolated from a low melting point agarose gel and made blunt with T4 DNA polymerase. The fragment, coding for amino acid residues 46-159 of OmpA, was ligated to the above pJG311 vector to make pTX101, which codes for the Lpp-OmpA-β-lactamase fusion. The ligation was transformed into E. coli strain JM109 made competent by the rubidium chloride method.

The Lpp-OmpA-β-lactamase was expressed from the strong lpp promoter which is inducible by IPTG (isopropyl thiogalactoside). Plasmid pTX101 also carries the lacI repressor. Although induction with IPTG resulted in high levels of protein production which are lethal to the cell, good expression was nevertheless obtained in the absence of inducer. Cultures were harvested in late exponential phase and the cells lysed and separated into soluble and cell envelope fractions by high speed centrifugation. Approximately 84% of total β-lactamase activity from JM109(pTX101) lysates was found in the cell envelope fraction. Essentially all the remaining activity was present in the soluble fraction of the cell lysates with less than 0.5% in the extracellular fluid. Even after prolonged incubation of stationary phase cells (24 hrs) there was no increase in the percentage of β-lactamase in the extracellular fluid, indicating that the fusion protein was not released from the cells, Figure 5. Qualitatively similar results were observed when the distribution of the fusion protein in the different fractions was examined by immunoblotting with β-lactamase or OmpA-specific antisera. The Lpp-β-lactamase protein from plasmid pJG311 had 2-fold higher total activities compared to the three-part fusion which contained the OmpA insert. This protein was also found predominantly in the membrane pellet (98% of total activity).

EXAMPLE 2

This example illustrates that a heterologous polypeptide prepared as in Example 1 is exposed to the external medium and retains activity.

Cell Fractionation

First it was demonstrated that the fusion protein was localized to the outer membrane. Cells were harvested from 200 ml of LB medium containing 0.2% glucose at an $A_{600}=1.0$, washed in 25 mM Tris-HCl (pH 7.4) and resuspended in 10 ml of the same buffer containing 1 mM EDTA and 100 μg/ml lysozyme at 4° C. After a 2 minute incubation the cells were lysed by two passages through a French pressure cell at 10,000 psi. The cellular debris was removed by centrifugation at $2,500 \times g$ for 8 minutes and the total membranes were spun down by centrifugation at $115,000 \times g$ for 1 hour. Membranes were resuspended in 0.8 ml of Tris-HCl buffer containing 25% sucrose and loaded onto a step gradient of 20, 35, 40, 45, 50 and 55% (w/w) sucrose. After centrifugation at $165,000 \times g$ for 16 hours in a Beckman SW41Ti rotor, 0.5 ml fractions were collected from the bottom of the tube. The density of the fractions was determined from refractive index measurements. The concentration of sucrose was lowered to <10% (w/w) by diluting the samples with Tris-HCl buffer followed by centrifugation to pellet the membranes.

Figure 2:
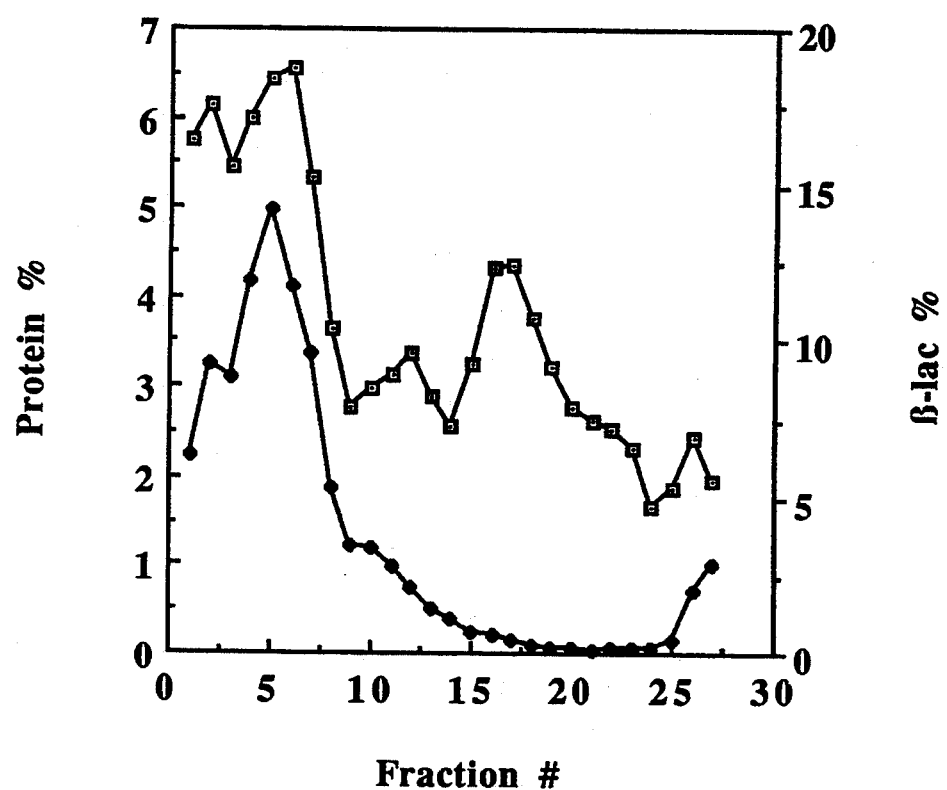
FIG. 2 shows the fractionation of membranes from JM109(pTX101) and JM109 cells. The percent of total membrane protein and $\beta$-lactamase activity in different fractions from a sucrose gradient of pTX101 is shown. $\beta$-lactamase activity was determined from the rate of hydrolysis of penicillin G. Fractions 2–7 had an average density of 1.22 g/cc, 11–13: $p=1.19$ g/cc and 16–20: $p=1.15$ g/cc corresponding exactly to the values for outer membrane, intermediate and inner membrane vesicles determined by Osborn.
Figure 3A:
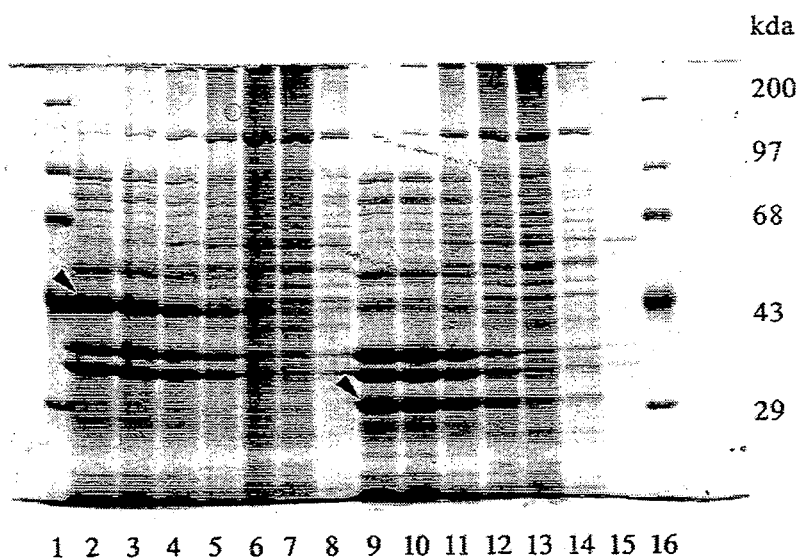
FIGS. 3A and 3B show fractionation on a sucrose gradient of membranes from JM109(pTX101) and JM109(pJG311).
Figure 3B:
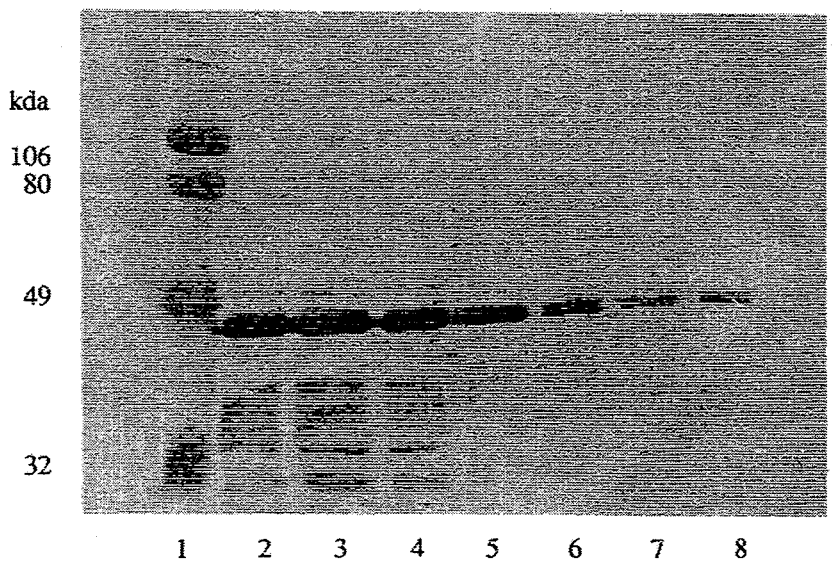

Two distinct protein peaks were obtained in fractions having the expected densities for inner and outer membrane vesicles (Osborn et al., 1972). Virtually all the β-lactamase enzymatic activity was found in the higher density fractions which corresponded to the outer membrane vesicles, FIG. 2. A protein band migrating at a molecular weight of approximately 43,000 daltons, the expected size of Lpp-OmpA-β-lactamase band was found and it was comparable in abundance to that of the major outer membrane proteins, FIG. 3A. The fusion protein was subjected to some degradation resulting in the appearance of lower molecular weight bands that crossreacted with β-lactamase-specific antibodies in immunoblots, FIG. 3B. The relatively small proportion of degradation fragments indicated that most of the fusion protein was not subjected to proteolysis.

Exposure of β-Lactamase on Cell Surface

Localization of the β-lactamase domain with respect to the external surface of E. coli was determined by various immunocytochemistry methods, activity assays and protease accessibility experiments. For immunofluorescence determinations, whole cells were labelled with rabbit β-lactamase-specific antibodies followed by secondary rhodamine-conjugated goat anti-rabbit antibodies. Washed, mid-exponential phase cells were resuspended in phosphate buffered saline (PBS) with or without 0.1 mg/ml trypsin and incubated at 37° C. Soybean trypsin inhibitor was added at different times to stop the reaction and incubation at 37° C. was continued for a total of 1 hour. All subsequent procedures were conducted at room temperature. The cells were washed with PBS, incubated for 45 minutes with PBS and 1% bovine serum albumin, washed and then incubated in the same PBS/BSA solution with rabbit anti-βlactamase antibodies at 1:1,000 dilution for 45 minutes. Following another three washes with PBS/BSA, the cells were mixed with rhodamine-conjugated goat anti-rabbit antibodies, incubated for 45 minutes and then washed three more times. Finally, the cells were resuspended in PBS and examined by phase contrast and video enhanced fluorescence microscope.

Figure 4A:
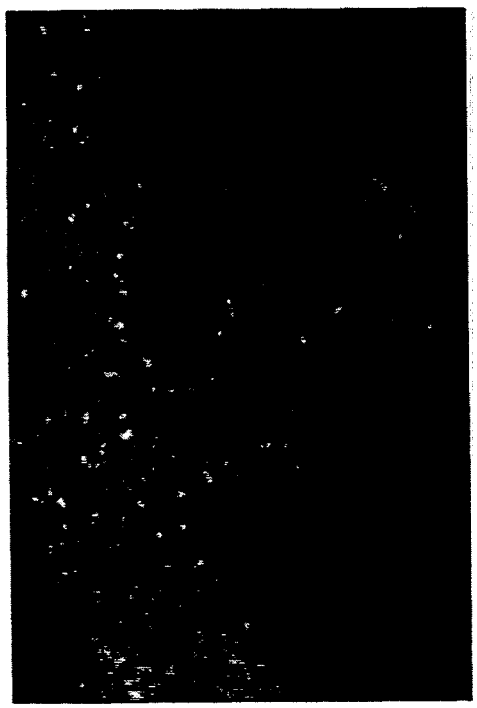
FIG. 4A shows a micrograph of JM109(pTX109) cells labeled with rabbit $\beta$-lactamase specific antibodies and rhodamine conjugated rabbit-specific antibodies viewed by fluorescence.
Figure 4B:
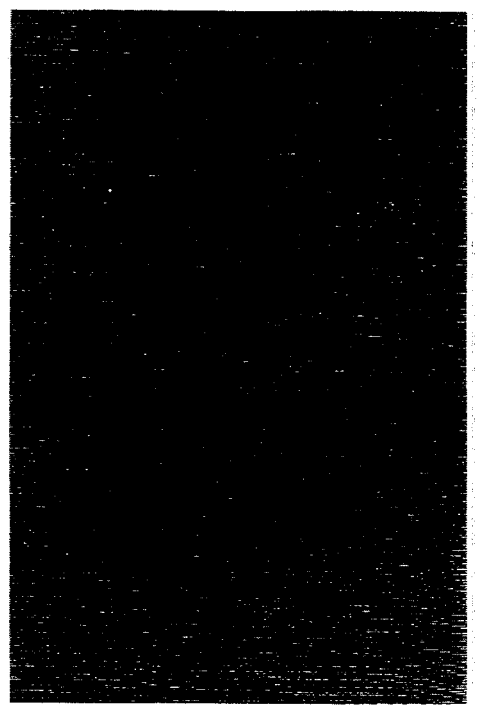
FIG. 4B shows the same field of cells viewed by phase contrast microscopy.

In control experiments, no fluorescence above background was detectable with JM109(pJG311) cells expressing the Lpp-β-lactamase fusion protein, indicating that there was no exportation to the outer surface. FIGS. 4A and 4B show a comparison of the same field of JM109(pTX101) cells viewed with fluorescence and phase contrast microscopies. Nearly all the cells became fluorescent, indicating sequences recognized by the anti-β-lactamase antibodies. Incubation with trypsin for various times prior to antibody labelling resulted in a gradual decrease in the fluorescent signal. After 1 hour of incubation no signal was detected.

Figure 9:
FIG. 9 shows a scanning electron micrograph of JM109(pTX101) cells labelled with anti-$\beta$-lactamase antibodies and secondary gold conjugated antibodies.

For immunoelectron microscopy cells were labelled with rabbit anti-β-lactamase specific antibodies, washed in various buffers as described above for the immunofluorescence experiments and reacted with secondary 30 nm diameter colloidal gold conjugated goat anti-rabbit antibodies. The labelled cells were positively stained with uranyl-acetate and viewed by scanning electron microscopy. In control experiments, no labelling occurred with JM109(pJG311) cells. FIG. 9 shows JM109(pTX101) cells so labelled, indicating the presence of sequences recognized by the anti-β-lactamase antibodies on the external surface.

The presence of enzymatically active β-lactamase on the cell surface was determined from protease accessibility experiments and the rates of hydrolysis of substrates not readily diffusible through the outer membrane. Cultures grown in M9 medium were harvested at $A_{600}=1.0$, washed with fresh medium and resuspended in M9 salts without glucose or antibiotics. The β-lactamase activity in the whole cells was determined using nitrocefin and penicillin G as substrates. The cells were incubated for 1 hr at 37° C. in the presence or absence of 0.1 mg/ml of either proteinase K or trypsin. The protease digestions were stopped by adding 10 mM phenylmethylsulfonyl fluoride or 0.2 mg/ml soybean trypsin inhibitor respectively. Subsequently, the cells were lysed and centrifuged at 2500×g for 8 min to remove unbroken cells. The membranes were pelleted as described above, resuspended in 50 mM potassium phosphate buffer, pH 6.5 and the remaining enzymatic activity measured.

In cells containing plasmid pTX101, approximately 20% of the total membrane-bound activity was reproducibly lost after a one hour incubation with either trypsin or proteinase K, compared with only a 3% decrease in JM109(pJG311), Table 1. A comparable, somewhat higher percentage of surface exposed activity was obtained from the rates of hydrolysis of nitrocefin in intact and lysed cells. Nitrocefin does not cross the outer membrane of E. coli and therefore can be used to test activity of extracellular β-lactamase (Kornacker and Pugsley, 1990). The rate of hydrolysis of nitrocefin by intact cultures of JM109(pJG311) was in agreement with results of protease accessibility studies, indicating Lpp-β-lactamase is not transported across the cell surface. Approximately 20-30% of the enzymatic activity of Lpp-OmpA-β-lactamase was surface exposed on cells grown at 37° C., a significant increase over the background in control cultures, see Table 1.

TABLE 1

Percent Surface Exposed β-Lactamase as Determined by Protease Accessibility and Enzymatic Activity Using Nitrocefin

| Plasmid | Temperature | Percent decrease in penicillin G hydrolysis following incubation with: | | Nitocefin activity in intact cells as percentage of total activity in membranes[b] |
|---|---|---|---|---|
| | | Proteinase K[a] | Trypsin[a,b] | |
| pJG311 | 37° C. | 3 | 3 | 6 |
| pTX101 | 37° C. | 23 | 18 | 38 |
| pTX101 | 24° C. | | 89 | 81 |

[a]Cells were incubated with proteinase K or trypsin for one hour and the total membrane fractions were isolated as described in the materials and methods sections. The percent of exposed β-lactamase corresponds to the activity remaining after incubation with proteases relative to untreated cells.
[b]The standard deviation for all experiments was less than ±5% of the reported mean values.

EXAMPLE 3

Figure 5:
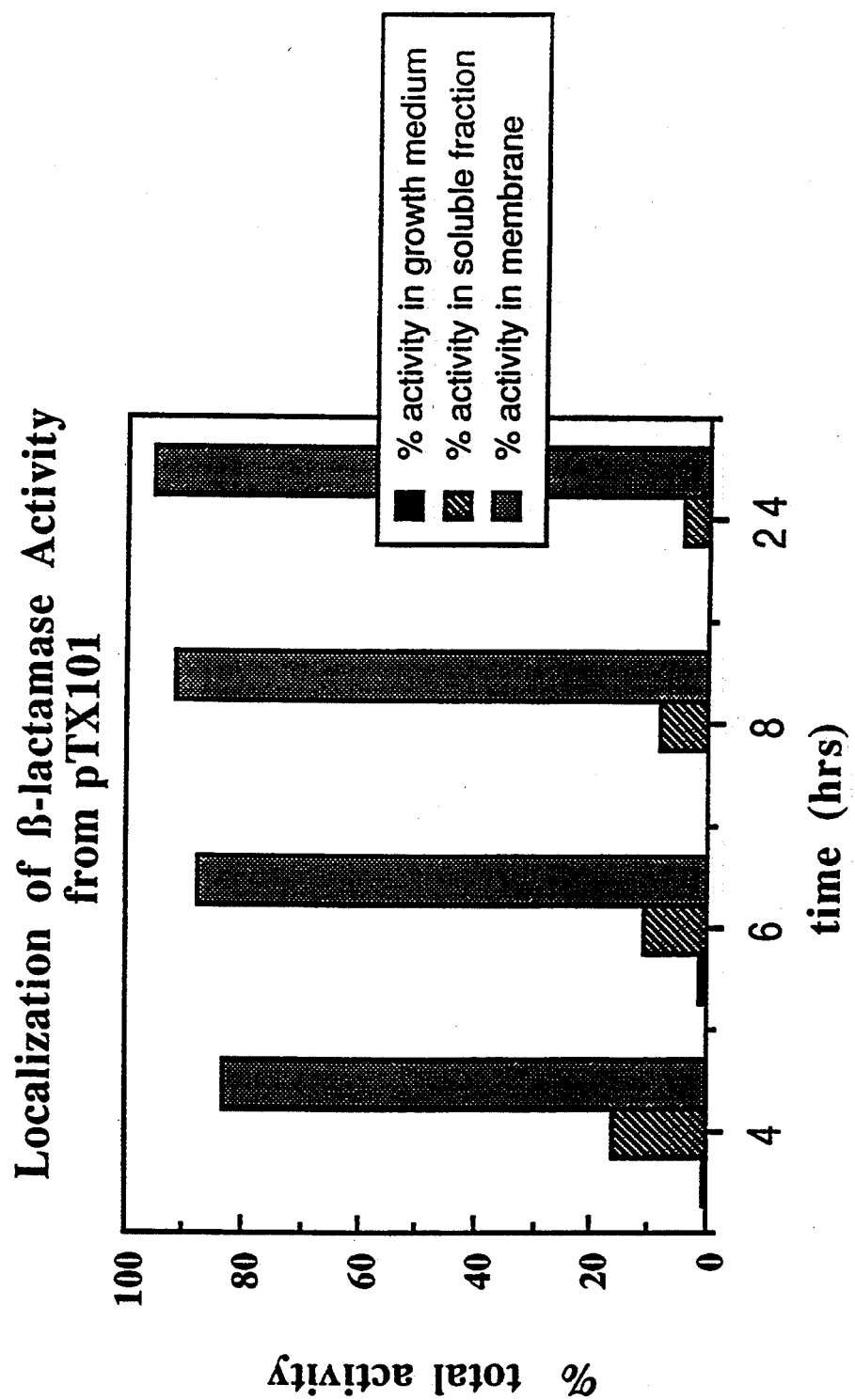
FIG. 5 shows the effect of extended incubation on measured $\beta$-lactamase activity of the tripartite fusion expressed on the outer membrane surface of E. coli.

The following example demonstrates that even after extended incubation, the region of the tripartite fusion containing the target protein remains stably anchored to the outer membrane of the host cell. This example demonstrates the surface stability of surface-expressed fusion polypeptides using the disclosed methods. Surface Stability of Translocated Fusion Protein β-Lactamase JM109 cells with the plasmid pTX101 were grown in LB supplemented with glucose and ampicillin. After 4, 6, 8 and 24 hours, 10 ml samples were collected and separated into culture supernatant, soluble and membrane fractions, FIG. 5. The cells were first pelleted by centrifugation at 8,000×g and the resulting supernatant was saved as the culture supernatant fraction. The pelleted cells were resuspended in 50 mM potassium phosphate buffer (pH 7) and lysed in a French pressure cell at 20,000 psi. The lysed samples were centrifuged at 2,500×g to pellet any unlysed cells and then centrifuged for 1 hr at 115,000×g. The supernatant from the high speed centrifugation was removed and saved as the soluble fraction and the pelleted membranes resuspended in 50 mM potassium phosphate buffer to obtain the membrane fractions. β-lactamase activity performed on the fractions indicated that even after prolonged incubation (24 hrs) the fusion was stably anchored to the outer membrane (FIG. 5).

EXAMPLE 4

This example illustrates that efficient surface-expression and maintenance of activity of surface-expressed polypeptides is affected by the culture temperature. The example is illustrated with β-lactamase, but effective surface expression with maintenance of function is also affected by temperature for alkaline phosphatase.

Effect of Temperature on β-Lactamase Expression and Activity

Cultures grown at 24° C. exhibited almost quantitative β-lactamase activity on the cell surface. The rate of nitrocefin hydrolysis and trypsin accessibility indicated 80–87% surface exposure, Table 1.

EXAMPLE 5

The following example illustrates expression of alkaline phosphatase on the outer membrane surface of *E. coli*. Alkaline phosphatase is a large dimeric enzyme with a monomer size of approximately 43,000 D. Disulfide bonds form rapidly after the protein has been exported from the cytoplasm. The expression of active protein on the bacterial surface indicates that there is no significant effect on the protein's ability to retain or fold to its native form after membrane translocation. This example also illustrates the versatility of the method in that alkaline phosphatase is a relatively large protein. In this example, tertiary and quaternary structures are unaffected by the expression.

Expression of Alkaline Phosphatase on *E. coli* Cell Surface

Plasmid pTX101 was cut with EcoRI at the unique site in the linker region between the OmpA and β-lactamase. Subsequently the DNA was treated with the Klenow fragment of DNA polymerase to create blunt ends. The phoA gene coding for the sequence of alkaline phosphatase was isolated from the plasmid pSWFII. A DNA fragment containing the phoA gene was obtained by cutting pSWFII with SbaI and then blunt-ended using the Klenow fragment. The linearized pTX101 vector and the phoA gene fragment were ligated overnight and the DNA was transformed into *E. coli* strain JM109. The new plasmid encoding the Lpp-OmpA-PhoA tripartite fusion was designated pTX1000. Exposure of the alkaline phosphatase on the surface of *E. coli* was tested by immunofluorescence microscopy using anti-alkaline phosphatase antibodies.

The degree of localization of alkaline phosphatase on the cell surface is expected to be enhanced in the strain JCB572 (Bardwell et al., 1991) which is deficient in the gene for the *E. coli* periplasmic protein disulfide isomerase, DsbA, and in cultures incubated at sub-optimal growth temperatures, for example 24° C.

PROPHETIC EXAMPLE 6

The present example outlines the procedure contemplated as useful for expressing an antibody on the surface of *E. coli*. The antibody used for illustration is a catalysic antibody capable of catalysis in addition to binding its cognate antigen. Although this example is illustrated with antibody 37C4 against a particular hapten, other high affinity antibodies could be surface-expressed in a like manner. The example shows how the disclosed methods could be used to prepare a single-chain $F_v$, that is, a recombinant protein composed of a $V_L$ chain linked to a $V_H$ chain with a polypeptide linker. This particular ScF$_v$ is a catalytic antibody.

Expression of Single-Chain F$_v$ Antibody on *E. coli* Cell Surface

Antibody 37C4 exhibits high binding against the hapten tris(4-methoxyphenyl)phosphonium (dissociation constant $>10^{-10}M^{-1}$. The antibody acts as a catalyst for the cleavage of various trityl ethers, increasing the reaction rate by about 200 fold compared to the uncatalyzed reaction in the absence of antibody. Total mRNA from the 37C4 hybridoma line is isolated and purified by standard techniques (Ausubel et al. 1987). The purified mRNA is used as a template for cDNA synthesis using a polymerase chain amplification technique (Sastry et al. 1989). The $V_L$ and the $V_H$ domains of the 37C4 antibody are cloned using suitable primers designed to introduce an in-frame EcoRI restriction site at the N-terminus of the $V_H$ and another one at the carboxy terminus of the $V_L$ for easy subcloning of the $F_v$ gene into the surface expression vector pTX101. Plasmid pTX101 contains a unique EcoRI site located at the downstream end of the DNA sequence for the OmpA domain and immediately before the beginning of the β-lactamase gene. An Lpp-OmpA-scF$_v$ tripartite fusion is constructed by digestion of pTX101 with EcoRI and ligation of the scF$_v$ fragment. The resulting plasmid is transformed into *E. coli* strain JM109. The presence of the single-chain antibody on the cell surface allows the cells to bind to a complex of tris(4-methoxyphenyl)phosphonium antigen linked to the protein avidin. The antigen is linked to avidin via its carboxy terminus by standard techniques (Staros et al. 1986). Finally, avidin is detected by immunofluorescence microscopy using anti-avidin antibodies conjugated to fluorescein (obtained from Vector Laboratories, Burlingame, Calif. Cells expressing the scF$_v$ fragment give a fluorescence signal whereas control *E. coli* do not.

PROPHETIC EXAMPLE 7

The present example outlines the procedure contemplated as useful for the selection of antibodies with high antigen binding affinity. The method is based on a selection procedure for recombinant antibody fragments on the surface of *E. coli*.

The method illustrated will overcome many of the problems currently associated with display of antibody molecules on phage surfaces. In particular, subcloning will not be necessary for production, the number of antibodies on the cell surface can be controlled and the greater flexibility in the design of the expression system will help ensure proper folding.

Selection of High Antigen Binding Affinity Antibodies Using a Cell Surface Display System BALB/C female mice (6–8 weeks old) are immunized with the hapten tris(4-methoxyphenyl)phosphonium coupled to Supercarrier (Pierce Chemical, Chicago, Ill.) dissolved in Freund's complete adjuvant administered intraperitoneally at a dose of 1 mg per animal. Follow up injections are given intramuscularly once per week for three weeks, rested 2 weeks and given a booster shot before checking for antibody production. Incomplete Freund's adjuvant is used for all injections subsequent to the first injection.

A library of single-chain $F_v$ antibodies is constructed using a polymerase chain reaction with total spleen mRNA from the immunized mice (Clarckson et al., 1991). The PCR primers are designed to introduce an in-frame EcoRI restriction site at the N-terminus of the $V_H$ and another restriction site at the carboxy terminus of the $V_L$ for easy subcloning of the $F_v$ gene into the surface expression vector pTX101. Subsequently, the library DNA is digested with EcoRI, a gene fragment of approximately 730 base pairs containing the entire $scF_v$ gene is identified. This DNA fragment is isolated and ligated to EcoRI digested plasmid pTX101. The ligation mixture is transformed into competent *E. coli* cells and transformants are selected on LB plates containing the antibiotic chloramphenicol. Plasmids in which the $scF_v$ is inserted in the correct orientation result in expression of tripartite fusion proteins in the order (from the amino terminus): Lpp-OmpA-$scF_v$. Colonies are pooled from the plate and grown in rich media at 23° C. to allow efficient localization of the $scF_v$ to the cell surface. Approximately $10^9$ cells are diluted in buffer to halt further growth and are loaded onto an affinity column (approx 5 ml bed vol) containing the immobilized hapten tris(4-methoxyphenyl)phosphonium. The column is washed with Tris-HCl buffer, pH 7.0. Bound cells are eluted by applying a linear gradient of the hapten. Elution of the cells from the column is directly related to the binding affinity of the exposed antibodies. This results in enrichment of high-binding affinity antibodies expressed on the surface of cells. The cells are collected, grown and used to prepare antibodies.

REFERENCES

The references listed below are incorporated herein by reference to the extent that they supplement, explain, provide a background for or teach methodology, techniques and/or compositions employed herein.

Agterberg, M., Adriaanse, H. and J. Tommassen, Gene 59, 145 (1987).
Barbas, C. F., Kang, A. S., Lerner, R. A. and Benovic, S. J., Proc. Natl. Acad. U.S.A. 88, 7978 (1991).
Bardwell, J. C. A., McGovern, K. & Beckwith, J., Cell, in print.
Bolivar et al., Gene, Z, 95 (1977).
Bosch, D. Leunissen, J., Verbakel, J., de Jong, M., van Erp, H., and Tommassen, J. J. Mol. Biol. 189, 449-455 (1986)
Bosch, D. Scholten, M., Verhagen, C. and Tommassen, J. Mol. Gen. Gener. 216, 144-148 (1989).
Breitling, F., Dübel, S., Seehaus, T., Klewinghaus, I. and Little, M., Gene 104, 147 (1991).
Chang et al., Nature 375, 615 (1978).
Charbit, A., Ronco, J., Michel. V., Weris, C., & Hofnung, M. (1991) J. Bacteriol. 173, 262-275.
Clarckson, T., Hoogenboom, H. R., Griffiths, A. D. and Winter, G., Nature 352 624 (1991).
De Libero G. and H. E>Kaufman, J. Immunol., 137, 2668 (1986).
Ehrmann, M., Boyd, D. and Beckwith, J., Proc. Nat'l. Acad. Sci. USA 87, 7574–7578 (1990).
Dougan, G., Smith, L. and F. Heffron, Adv. Veter. Sci. Compar. Med 33, 271 (1989).
Filloux, A., Bally, M., Ball, G., Akrim, M., Tommassen, J., & Lazdunski, A. (1990) EMBO J. 9, 4323–4329.
Freudl, R., Schwarz, H., Klose, M., Movva, N. R., & Henning, U., EMBO J, 4, 3593-3598 (1985).
Freudl, R., Gene 82, 229-236 (1989).
Goeddel et al., Nature, 281 544 (1979).
Ghrayeb, J., & Inouye, M. (1984) J. Biol. Chem. 259, 463–467.
Huse, W. D., Sastry, L., Iverson, S. A., Kang, A. S., Alting-Mees, M., Burton, D. R., Benkovic, S. J. and R. A. Lerner, Science 246, 1275 (1989).
Inukai, M., Coleman, J., & Inouye, M., manuscript in preparation.
Itakura et al, Science 198, 1056 (1977).
Jacobs, F. A., Romeyer, F. M., Beauchemin, M. and R. Brousseau, Gene 83, 95 (1989).
Klose, J., Schwarz, H., MacIntyre, S., Freudl, R., Eschbach, M., & Henning, U. (1988) J. Biol. Chem. 263, 13291–13296.
Klose, M., MacIntyre, S., Schwarz, H., & Henning, U. (1988), J. Biol. Chem. 263, 13297–13302.
Kornacker, M. G., & Pugsley, A. P., (1990) Mol. Microbiol. 4, 73–85.
Kornacker, M. G. and Pugsley, A. P., Mol. Microbiology 4, 1101–1109 (1990).
Kronvall, G., Simons, A., Myhre, E. B. and S. Jonssson, Infect. Immunol., 25, 1 (1979).
Mattiason B and T Ling, in "Bioprocess Technology, v. 1", McGregor, W. C. (ed.), Dekker, New York, (1986).
Mohr, P. and K. Pommerening, Affinity Chromatography, Practical and Theoretical Aspects,"Marcel-Dekker, New York (1986).
Murphy, C. K., Kalve, V. I., & Klebba, P. E. (1990) J. Bacteriol. 172, 2736-2742.
Newton, S. M. C., Jacob, C. O. and B. A. D. Stocker, Science, 244, 70 (1989).
O'Callaghan, C. H., Morris, A., Kirby, S. M., & Shingler, A. H. (1972) Antimicrob. Ag. Chemother 1, 283–288.
Orlandi, R., Gussow, D. H., Jones, P. T. and G. Winter, Proc. Natl. Acad. Sci. U.S.A., 86, 3833 (1989).
Powell, J. D., Kilpatrick, P. K. and R. Carbonell, Biotechnol. Bioeng., 33, 173 (1989).
Samuni, A. (1975) Anal. Biochem. 63, 17.
Sastry et al., Proc. Natl. Acad. Sci. U.S.A., 86, 5728 (1989).
Siebwenlist et al., Cell 20, 269 (1980).
Skerra A. and A. Pluckthun, Science, 240, 1038 (1988).
Stover et al., Nature, 351, 456 (1991).
Tampion, J. and M. D. Tampion, "Immobilized Cells and Enzymes: a Practical Approach," Cambridge University Press, Canbridge (1987).
Thiry, G., Clippe. A., Scarcez, T. and J. Petre, Appl. Environ. Microbiol. 55, 984 (1989).
Tsao, I. F., Shipman, C. and H. Y. Wang, Bio/Technology, 6, 1330 (1988).
Turkova, J., "Affinity Chromatography," Elsevier, Amsterdam (1978).
Vieira, J., & Messing, J., Gene 19, 259–268 (1982).
Yamaguchi, K., Yu, F., & Inouye, M., Cell 53, 423–432 (1988).
Yoshihiro, M., Coleman, J., & Inouye, M., in Experimental Manipulation of Gene Expression, (Inouye, M., ed) 15–32, Academic Press, New York (1983).

What is claimed is:

1. A recombinant DNA for expressing a polypeptide stably anchored on the external surface of the outer membrane of E. coli or Salmonella comprising:
   (A) A Salmonella or E. coli lipoprotein 5' gene segment which encodes at least the signal peptide and at least the first three amino acids of the mature protein;
   (B) A DNA segment encoding a transmembrane outer membrane protein selected from the group consisting of OmpA, OmpC, OmpF and OmpT of E. coli or Salmonella; and
   (C) A DNA segment encoding a desired soluble heterologous or homologous polypeptide not normally found in the outer membrane of gram negative bacteria wherein DNA (A) is linked 5' to DNA (B) and DNA (B) is linked 5' to DNA (C), all operatively linked with a promoter sequence to express and anchor the desired polypeptide on the external bacterial surface.

2. A recombinant DNA vector comprising:
   An E. coli or Salmonella lipoprotein 5' gene segment which encodes the signal peptide and at least the first three amino acids of the mature protein;
   A DNA segment encoding a transmembrane outer membrane protein selected from the group consisting of OmpA, OmpT, OmpF and OmpC of E. coli or Salmonella; and
   A polylinker DNA segment into which a DNA encoding soluble heterologous or homologous polypeptide not normally found in the outer membrane of gram-negative bacteria may be inserted, all being operatively linked 5' to 3' with a promoter sequence to express and stably anchor the polypeptide to the external bacterial surface.

3. The recombinant DNA of claim 1 or the recombinant vector of claim 2 wherein the lipoprotein gene segment comprises the 5' segment of a gene selected from a group consisting of osmB, traT, NlpB, and Psuedomonas lipoprotein 1.

4. The recombinant DNA of claim 1 or the recombinant vector of claim 2 wherein the DNA encoding the lipoprotein gene segment encodes the N-terminal amino acid residues of FIG. 7 (SEQ ID NO. 1) at base pair positions 1-87.

5. The recombinant DNA of claim 1 or the recombinant vector of claim 2 wherein the transmembrane protein domain comprises an amino acid sequence of FIG. 7 (SEQ ID NO. 1) at base pairs 94-435.

6. The recombinant DNA of claim 1 or the recombinant vector of claim 2 wherein the promoter is an inducible promoter.

7. The recombinant DNA or the recombinant vector of claim 6 wherein the inducible promoter is Lpp or lac promoter.

8. An *Escherichia coli* transformed with a vector containing the DNA of claim 1.

9. A Salmonella transformed with a vector containing the DNA of claim 1.

10. A method of preparing a functional polypeptide stably anchored on the external surface of the outer membrane of a bacterial cell comprising growing the bacterial host cell of claim 8 or claim 9 under conditions permitting DNA expression and protein production followed by recovering the stably anchored polypeptide so produced.

11. The method of claim 10 wherein the growing is conducted between about 22° C. and 40° C.

12. The method of claim 10 wherein the growing is conducted at about 24° C.

13. The recombinant DNA of claim 1 wherein the soluble homologous polypeptide is β-lactamase or alkaline phosphatase.

14. The recombinant DNA of claim 1 wherein the heterologous polypeptide is a single chain antibody or antibody fragment.

15. A kit for use in preparing transformed E. coli or Salmonella comprising an expression vector that includes the recombinant DNA of claim 1.

16. The kit of claim 15 wherein the expression vector has the sequence shown in FIG. 7 (SEQ ID NO: 1).

17. The kit of claim 15 wherein the expression vector is provided in lyophilized form or in a suitable buffer.

18. The recombinant DNA of claim 1 wherein the heterologous polypeptide is cellulose binding domain of cellulase.

19. The recombinant DNA of claim 1 wherein the encoded transmembrane protein is a transmembrane sequence of OmpA.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 1273 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

```
ATGAAAGCTA CTAAACTGGT ACTGGGCGCG GTAATCCTGG GTTCTACTCT GCTGGCAGGT        60
TGCTCCAGCA ACGCTAAAAT CGATCAGGGA ATTAACCCGT ATGTTGGCTT TGAAATGGGT       120
TACGACTGGT TAGGTCGTAT GCCGTACAAA GGCAGCGTTG AAAACGGTGC ATACAAAGCT       180
CAGGGCGTTC AACTGACCGC TAAACTGGGT TACCCAATCA CTGACGACCT GGACATCTAC       240
ACTCGTCTGG GTGGCATGGT ATGGCGTGCA GACACTAAAT CCAACGTTTA TGGTAAAAAC       300
CACGACACCG GCGTTTCTCC GGTCTTCGCT GGCGGTGTTG AGTACGCGAT CACTCCTGAA       360
ATCGCTACCC GTCTGGAATA CCAGTGGACC AACAACATCG GTGACGCACA CCATCGGC         420
ACTCGTCCGG ACAACGGAAT TCCGGGTCAC CCAGAAACGC TGGTGAAAGT AAAAGATGCT       480
GAAGATCAGT TGGGTGCACG AGTGGGTTAC ATCGAACTGG ATCTCAACAG CGGTAAGATC       540
CTTGAGAGTT TTCGCCCCGA AGAACGTTTT CCAATGATGA GCACTTTTAA AGTTCTGCTA       600
TGTGGCGCGG TATTATCCCG TGTTGACGCC GGGCAAGAGC AACTCGGTCG CCGCATACAC       660
TATTCTCAGA ATGACTTGGT TGAGTACTCA CCAGTCACAG AAAAGCATCT TACGGATGGC       720
ATGACAGTAA GAGAATTATG CAGTGCTGCC ATAACCATGA GTGATAACAC TGCGGCCAAC       780
TTACTTCTGA CAACGATCGG AGGACCGAAG GAGCTAACCG CTTTTTTGCA ACATGGGG        840
GATCATGTAA CTCGCCTTGA TCGTTGGGAA CCGGAGCTGA ATGAAGCCAT ACCAAACGAC       900
GAGCGTGACA CCACGATGCC TGCAGCAATG GCAACAACGT TGCGCAAACT ATTAACTGGC       960
GAACTACTTA CTCTAGCTTC CCGGCAACAA TTAATAGACT GGATGGAGGC GGATAAAGTT      1020
GCAGGACCAC TTCTGCGCTC GGCCCTTCCG GCTGGCTGGT TTATTCGTGA TAAATCTGGA      1080
GCCGGTGAGC GTGGGTCTCG CGGTATCATT GCAGCACTGG GGCCAGATGG TAAGCCCTCC      1140
CGTATCGTAG TTATCTACAC GACGGGGAGT CAGGCAACTA TGGATGAACG AAATAGACAG      1200
ATCGCTGAGA TAGGTGCCTC ACTGATTAAG CATTGGTAAC TGTCAGACCA AGTTTACTCA      1260
TATATACTTT AGA                                                        1273
```

( 2 ) INFORMATION FOR SEQ ID NO:2:

( i ) SEQUENCE CHARACTERISTICS:
    ( A ) LENGTH: 1273 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

```
ATG AAA GCT ACT AAA CTG GTA CTG GGC GCG GTA ATC CTG GGT TCT ACT CTG        51
Met Lys Ala Thr Lys Leu Val Leu Gly Ala Val Ile Leu Gly Ser Thr Leu
1               5                   10                  15

CTG GCA GGT TGC TCC AGC AAC GCT AAA ATC GAT CAG GGA ATT AAC CCG TAT       102
Leu Ala Gly Cys Ser Ser Asn Ala Lys Ile Asp Gln Gly Ile Asn Pro Tyr
            20                  25                  30

GTT GGC TTT GAA ATG GGT TAC GAC TGG TTA GGT CGT ATG CCG TAC AAA GGC       153
```

```
Val Gly Phe Glu Met Gly Tyr Asp Trp Leu Gly Arg Met Pro Tyr Lys Gly
 35              40                  45                  50

AGC GTT GAA AAC GGT GCA TAC AAA GCT CAG GGC GTT CAA CTG ACC GCT AAA    204
Ser Val Glu Asn Gly Ala Tyr Lys Ala Gln Gly Val Gln Leu Thr Ala Lys
             55                  60                  65

CTG GGT TAC CCA ATC ACT GAC GAC CTG GAC ATC TAC ACT CGT CTG GGT GGC    255
Leu Gly Tyr Pro Ile Thr Asp Asp Leu Asp Ile Tyr Thr Arg Leu Gly Gly
         70                  75                  80                  85

ATG GTA TGG CGT GCA GAC ACT AAA TCC AAC GTT TAT GGT AAA AAC CAC GAC    306
Met Val Trp Arg Ala Asp Thr Lys Ser Asn Val Tyr Gly Lys Asn His Asp
                 90                  95                 100

ACC GGC GTT TCT CCG GTC TTC GCT GGC GGT GTT GAG TAC GCG ATC ACT CCT    357
Thr Gly Val Ser Pro Val Phe Ala Gly Gly Val Glu Tyr Ala Ile Thr Pro
            105                 110                 115

GAA ATC GCT ACC CGT CTG GAA TAC CAG TGG ACC AAC AAC ATC GGT GAC GCA    408
Glu Ile Ala Thr Arg Leu Glu Tyr Gln Trp Thr Asn Asn Ile Gly Asp Ala
120                 125                 130                 135

CAC ACC ATC GGC ACT CGT CCG GAC AAC GGA ATT CCG GGT CAC CCA GAA ACG    459
His Thr Ile Gly Thr Arg Pro Asp Asn Gly Ile Pro Gly His Pro Glu Thr
            140                 145                 150

CTG GTG AAA GTA AAA GAT GCT GAA GAT CAG TTG GGT GCA CGA GTG GGT TAC    510
Leu Val Lys Val Lys Asp Ala Glu Asp Gln Leu Gly Ala Arg Val Gly Tyr
        155                 160                 165                 170

ATC GAA CTG GAT CTC AAC AGC GGT AAG ATC CTT GAG AGT TTT CGC CCC GAA    561
Ile Glu Leu Asp Leu Asn Ser Gly Lys Ile Leu Glu Ser Phe Arg Pro Glu
                175                 180                 185

GAA CGT TTT CCA ATG ATG AGC ACT TTT AAA GTT CTG CTA TGT GGC GCG GTA    612
Glu Arg Phe Pro Met Met Ser Thr Phe Lys Val Leu Leu Cys Gly Ala Val
            190                 195                 200

TTA TCC CGT GTT GAC GCC GGG CAA GAG CAA CTC GGT CGC CGC ATA CAC TAT    663
Leu Ser Arg Val Asp Ala Gly Gln Glu Gln Leu Gly Arg Arg Ile His Tyr
205                 210                 215                 220

TCT CAG AAT GAC TTG GTT GAG TAC TCA CCA GTC ACA GAA AAG CAT CTT ACG    714
Ser Gln Asn Asp Leu Val Glu Tyr Ser Pro Val Thr Glu Lys His Leu Thr
            225                 230                 235

GAT GGC ATG ACA GTA AGA GAA TTA TGC AGT GCT GCC ATA ACC ATG AGT GAT    765
Asp Gly Met Thr Val Arg Glu Leu Cys Ser Ala Ala Ile Thr Met Ser Asp
        240                 245                 250                 255

AAC ACT GCG GCC AAC TTA CTT CTG ACA ACG ATC GGA GGA CCG AAG GAG CTA    816
Asn Thr Ala Ala Asn Leu Leu Leu Thr Thr Ile Gly Gly Pro Lys Glu Leu
                260                 265                 270

ACC GCT TTT TTG CAC AAC ATG GGG GAT CAT GTA ACT CGC CTT GAT CGT TGG    867
Thr Ala Phe Leu His Asn Met Gly Asp His Val Thr Arg Leu Asp Arg Trp
            275                 280                 285

GAA CCG GAG CTG AAT GAA GCC ATA CCA AAC GAC GAG CGT GAC ACC ACG ATG    918
Glu Pro Glu Leu Asn Glu Ala Ile Pro Asn Asp Glu Arg Asp Thr Thr Met
290                 295                 300                 305

CCT GCA GCA ATG GCA ACA ACG TTG CGC AAA CTA TTA ACT GGC GAA CTA CTT    969
Pro Ala Ala Met Ala Thr Thr Leu Arg Lys Leu Leu Thr Gly Glu Leu Leu
            310                 315                 320

ACT CTA GCT TCC CGG CAA CAA TTA ATA GAC TGG ATG GAG GCG GAT AAA GTT   1020
Thr Leu Ala Ser Arg Gln Gln Leu Ile Asp Trp Met Glu Ala Asp Lys Val
        325                 330                 335                 340

GCA GGA CCA CTT CTG CGC TCG GCC CTT CCG GCT GGC TGG TTT ATT CGT GAT   1071
Ala Gly Pro Leu Leu Arg Ser Ala Leu Pro Ala Gly Trp Phe Ile Ala Asp
                345                 350                 355

AAA TCT GGA GCC GGT GAG CGT GGG TCT CGC GGT ATC ATT GCA GCA CTG GGG   1122
Lys Ser Gly Ala Gly Glu Arg Gly Ser Arg Gly Ile Ile Ala Ala Leu Gly
            360                 365                 370

CCA GAT GGT AAG CCC TCC CGT ATC GTA GTT ATC TAC ACG ACG GGG AGT CAG   1173
Pro Asp Gly Lys Pro Ser Arg Ile Val Val Ile Tyr Thr Thr Gly Ser Gln
375                 380                 385                 390
```

```
GCA ACT ATG GAT GAA CGA AAT AGA CAG ATC GCT GAG ATA GGT GCC TCA CTG   1224
Ala Thr Met Asp Glu Arg Asn Arg Gln Ile Ala Glu Ile Gly Ala Ser Leu
            395             Arg     400                 405

ATT AAG CAT TGG TAACTGTCAG ACCAAGTTTA CTCATATATA CTTTAGA              1273
Ile Lys His Trp
    410     412
```